United States Patent
Hoyland et al.

[11] Patent Number: 6,013,802
[45] Date of Patent: Jan. 11, 2000

[54] FLUORESCENT CONJUGATES OF METAL-CHELATING NITROGEN HETEROCYCLES

[75] Inventors: Brian Matthew Hoyland; Michael A. Kuhn; Richard P. Haugland, all of Eugene, Oreg.

[73] Assignee: Molecular Probes, Inc., Eugene, Oreg.

[21] Appl. No.: 08/798,390

[22] Filed: Feb. 7, 1997

Related U.S. Application Data

[62] Division of application No. 08/384,945, Feb. 6, 1995, Pat. No. 5,648,270.

[51] Int. Cl.[7] .................................................. C07D 401/00
[52] U.S. Cl. .......................... 546/18; 546/42; 546/47; 546/256; 546/257; 546/266; 546/268.1; 546/281.7
[58] Field of Search .................... 546/17, 18, 42, 546/47, 255, 256, 257, 261, 262, 263, 266, 268.1, 281.7

[56] References Cited

U.S. PATENT DOCUMENTS

| | | |
|---|---|---|
| 4,603,209 | 7/1986 | Tsien et al. . |
| 4,774,339 | 9/1988 | Haugland et al. . |
| 4,849,362 | 7/1989 | DeMarinis et al. . |
| 4,945,171 | 7/1990 | Haugland et al. . |
| 5,049,673 | 9/1991 | Tsien et al. . |
| 5,134,232 | 7/1992 | Tsien et al. . |
| 5,135,717 | 8/1992 | Renzoni et al. . |
| 5,227,487 | 7/1993 | Haugland et al. . |
| 5,268,486 | 12/1993 | Waggoner et al. . |
| 5,274,113 | 12/1993 | Kang et al. . |
| 5,405,975 | 4/1995 | Kuhn et al. . |
| 5,433,896 | 7/1995 | Kang et al. . |
| 5,453,517 | 9/1995 | Kuhn et al. . |
| 5,459,276 | 10/1995 | Kuhn et al. . |
| 5,501,980 | 3/1996 | Katerinopoulos et al. . |

FOREIGN PATENT DOCUMENTS

| | | |
|---|---|---|
| 0277139 B1 | 8/1990 | European Pat. Off. . |
| 91/18006 | 11/1991 | WIPO . |

OTHER PUBLICATIONS

Martel, et al., Critical Stability Constants, vol. 1, Plenum Press, New York (1974).
Guilbault, Practical Fluorescence, 2$^{nd}$ Ed., Marcel Dekker, Pub. (1990).
Haugland, Molecular Probes Handbook of Fluorescent Probes and Research Chemicals (1992).
Bissel, et al., Chem. Soc. Rev. 187 (1992).
Brinkley, Bioconj. Chem. 3,2 (1992).
Org. Synth 2, 15 (1943).

*Primary Examiner*—Gary Geist
*Assistant Examiner*—Jean F Vollano
*Attorney, Agent, or Firm*—Allegra J. Helfenstein; Anton E. Skaugset

[57] ABSTRACT

The present invention describes a family of fluorescent indicators for metal cations. The indicators are fluorophore conjugates of pyridyl-based metal ion chelators. The indicators are very sensitive detection as quantification reagents for a variety of metals, in a variety of oxidation states, even in the presence of high concentrations of $Ca^{2+}$, $Na^+$, or $K^+$ or other ions, such as is found in seawater, making them highly useful for assaying physiological samples, biological samples, or environmental samples.

18 Claims, 9 Drawing Sheets

FLUORESCENT CONJUGATES OF METAL-CHELATING NITROGEN HETEROCYCLES

This application is a division of U.S. application Ser. No. 08/384,945 filed Feb. 6, 1995, now U.S. Pat. No. 5,648,270.

This invention was made with U.S. Government support under research contract no. N00014-C-0270 awarded by the U.S. Office of Naval Research. The U.S. Government has certain rights to this invention.

FIELD OF THE INVENTION

The invention relates to novel fluorescent indicators that are useful for the detection, discrimination and quantification of metal cations. Tile indicators are fluorescent conjugates of pyridyl-based metal ion-chelating groups that can be used to determine the presence of small amounts of selected metal ions, in the presence of other metal ions.

BACKGROUND

Metal ions are ubiquitous in nature and are essential components of all biological systems. Cells utilize metal ions for a wide variety of functions, such as messengers, gas carriers, catalysts, templates for polymer formation and regulatory elements for gene transcription.

Due to their importance and prevalence in industrial applications and manufacturing, metals have also become a major source of environmental contamination. The most toxic metal ions in environmental samples are those that are readily soluble in water. Unfortunately, current detection methods for soluble metal ions require bulky or sensitive instrumentation, making measurements in the field impractical. As a result, environmental samples must currently be transported to an analytical laboratory, resulting in a greater potential for contamination or sample degradation during storage. It is known that storage can alter the metal-ion concentration of a sample through adsorption of the metal on the surface of the container, or by the growth of microorganisms that can alter the speciation of metal ions in the sample. Fluorescent reagents that can simply and cheaply detect a variety of metal ions, including the ability to differentiate different oxidation states of the same metal ion, in a variety of solutions (biological, environmental, industrial), would provide an economical and reliable means for the detection of such environmental contaminants in the field.

Metal chelators that contain heteroaromatic nitrogen atoms are well known in the scientific literature, and the stability constants and properties of these chelators have been thoroughly reviewed and compiled (e.g. Martel et al., CRITICAL STABILITY CONSTANTS, VOL. 1, Plenum Press, New York (1974)). Molecules with heterocyclic nitrogen binding sites are widely used as analytical tools for extracting metal ions into organic solvents. Chemists currently take advantage of the extreme water insolubility of the majority of these chelators to preconcentrate metal ions in organic solvents prior to atomic absorption spectroscopy or colorimetric detection. However, these chelators are generally not water soluble and could not be used in biological systems. Further, they do not function as fluorescent indicators for the metal ions they complex.

Fluorescent indicators for metal ions that comprise a nitrogen-containing heterocycle as the ion binding site and an additional covalently attached fluorophore as a responding element have not been described in the literature. While a variety of fluorescent indicators that are useful for the detection of biologically relevant soluble free metal ions (such as $Ca^{2+}$, $Mg^{2+}$ and $Zn^{2+}$) have been described, these indicators utilize oxygen-containing anionic or polyanionic chelators to bind to metal ions. In particular, fluorescent indicators utilizing a polycarboxylate BAPTA chelator have been previously described (U.S. Pat. No. : 4,603,209 to Tsien et al. (1986); U.S. Pat. No. 5,049,673 to Tsien et al. (1991); U.S. Pat. No. 4,849,362 to DeMarinis et al. (1989); U.S. Pat. No. 5,453,517 to Kuhn et al. (1995); U.S. Pat. No. 5,501,980 to Malekzadeh et al. (1996); U.S. Pat. No. 5,459,276 to Kuhn et al. (1995). While some of these known indicators have been used to detect divalent or trivalent ions other than $Ca^{2+}$ or $Mg^{2+}$, previously known polycarboxylate fluorescent metal ion chelators usually suffer from high sensitivity to micromolar concentrations of $Ca^{2+}$ ion, or millimolar concentrations of $Na^+$ or $K^+$. This is an extreme drawback when it is desirable to detect extremely small concentrations of metal ions in the presence of other metal ions, such as in biological fluids or sea water, or any sample that contains $Ca^{2+}$, $Na^+$ or $K^+$. These fluorescent indicators are consequently unable to discriminate toxic metal contamination in the presence of these common ions. Several fluorescent indicators selective for $Li^+$, $Na^+$ and $K^+$ in aqueous or organic solution have been described, but their metal binding and ability to discriminate ions has usually been based on the chemical modification of crown ethers (U.S. Pat. No. 5,134,232 to Tsien et al. (1992); U.S. Pat. No. 5,405,975 to Kuhn et al. (1995).

A wide variety of other metal complexing agents that either yield fluorescent metal complexes or have their intrinsic fluorescence quenched by complexing with a metal have been described. These have been extensively reviewed by Guilbault in PRACTICAL FLUORESCENCE, 2nd Edition, Marcel Dekker, Publishers (1990). Many of these reagents require extraction of the metal into an organic solvent prior to its detection or quantification. Also, metal detection by many of the reagents involves a reduction in fluorescence of the reagent rather than the experimentally preferred enhancement of fluorescence. Metals have been determined by the selective extraction of the ternary complex of a metal, a fluorophore and a complexing agent into an organic solvent. This method differs from the subject invention both in requiring a three component mixture of reagents and in requiring extraction into an organic solvent. Metal complexes of certain reagents, including phenanthridines and bipyridyls, are intrinsically luminescent, particularly in organic solvents, as a result of emission transitions of the metal itself and the complexing agent primarily serves to protect the metal from quenching by solvent and to absorb the exciting light. These are typically complexes of ruthenium or certain rare earth metals. Various methods recommended for detection of metals by the catalytic formation of a fluorescent product differ from the instant method in that such catalytic methods lack a rapid and reversible response.

In general, a useful property for metal ion indicators is the ability to detect and/or quantify a selected metal ion in the presence of other metal ions. While discrimination from $Ca^{2+}$, $Na^+$ and $K^+$ ions (as discussed above) is useful for certain biological or environmental samples, the ability to discriminate other metal ions is also useful. In particular, an indicator that could differentiate between different oxidation states of a single metal would be very useful for detecting oxidative or reductive activity. For example, the detection of $Fe^{2+}$ in the presence of $Fe^{3+}$, or the detection of $Cu^+$ in the presence of $Cu^{2+}$.

The indicators of the present invention allow the direct measurement of trace concentrations of selected metal ions in solution, including the measurement of specific oxidation states. The indicators described are insensitive to high concentrations of monovalent and divalent ions commonly found in seawater and biological fluids, and therefore can be used to assay metal ions such as $Hg^{2+}$, $Pb^{2+}$ or $Cu^{2+}$ in the range of $10^{-6}$ to $10^{-9}$ molar, or lower, even in the presence of high concentrations of $Ca^{2+}$, $Mg^{2+}$, $K^+$, $Na^+$ and $Cl^-$. The sensitivity and discrimination of the instant indicators lets solution assays be performed without requiring preconcentration or other manipulations of the sample. The need to manipulate the sample in this way when using other, less sensitive detection reagents, is one of the main sources of error in determining metal contamination of environmental samples. Finally, several of the indicators of the present invention allow the researcher to detect metal ions using only ambient light or low cost, battery powered UV excitation sources, ideally suited for field conditions. The indicators are therefore highly useful for on-site environmental testing eliminating the difficulties associated with sampling, sample transportation and sample storage.

In general, the fluorescent indicators of the present invention serve as direct, sensitive probes for heavy metal ions at the very low (parts-per-million (ppm), parts-per-billion (ppb)) concentrations generally associated with deleterious biological effects and environmental regulation.

SUMMARY OF THE INVENTION AND DESCRIPTION OF PREFERRED EMBODIMENTS

Figure 1:
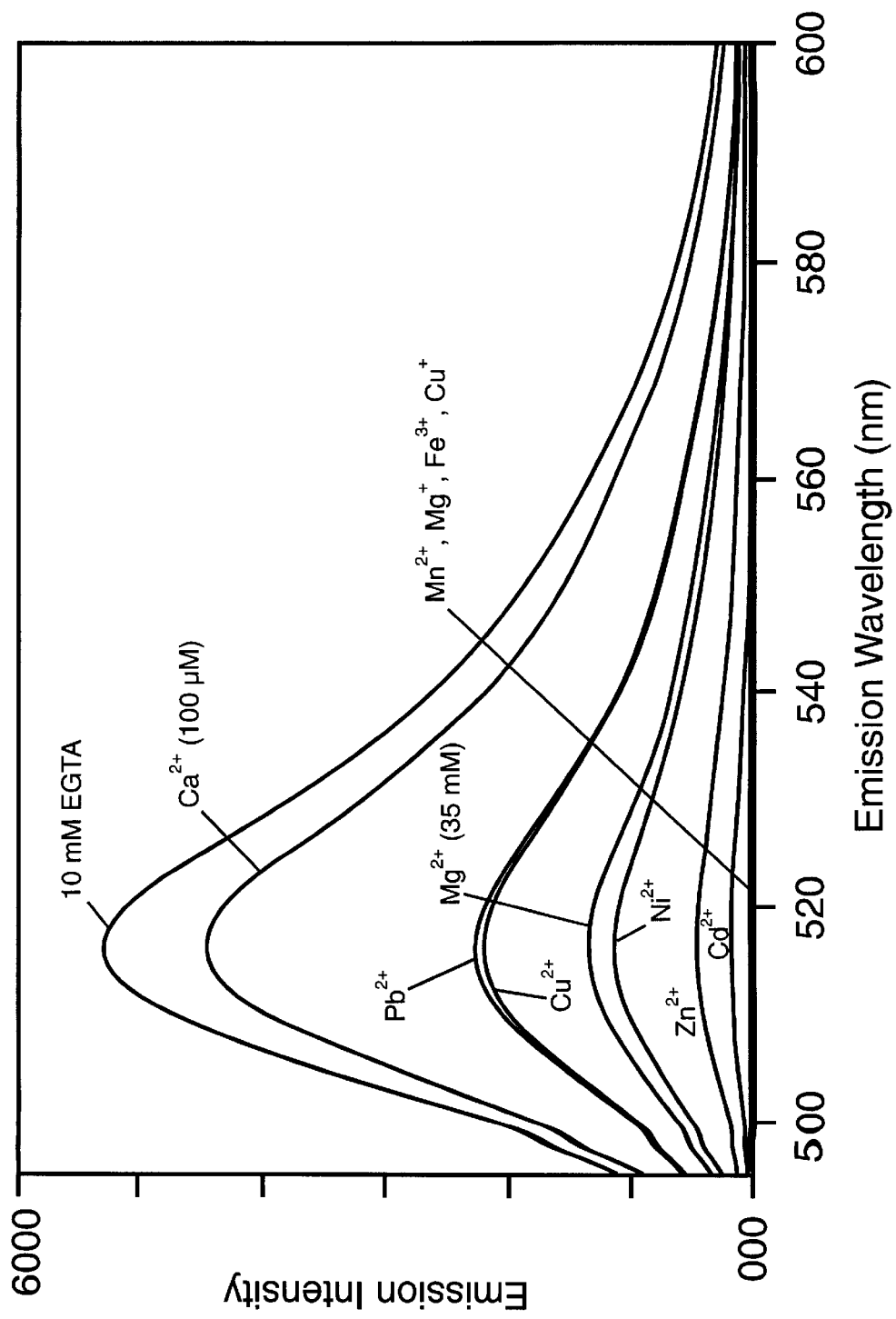
FIG. 1: The relative fluorescence emission intensity of a fluorescein conjugate of 5-amino-1,10-phenanthroline in response to selected metal ions.

The invention relates to a method of determining the presence of metal ions in solution using fluorescent conjugates, including novel fluorescent conjugates. The fluorescent conjugates of the invention exhibit a detectable change in fluorescence response upon binding metal cations.

The fluorescent conjugates used to practice the invention are composed of a metal ion-binding moiety that is covalently linked to one or two fluorophores, which may be the same or different. The linkage-fluorophore combination is herein represented by the substituent —L—$F_L$, where $F_L$ is a fluorophore, and L is a covalent linkage that attaches the metal ion-binding moiety to the fluorophore.

The Metal Ion Binding Moiety

The metal ion binding moiety (M) possesses at least two pyridyl rings, according to the general formula

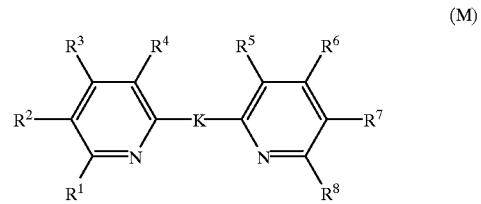

where the pyridyl rings have the primary ring substituents $R^1$, $R^2$, $R^3$, $R^4$, $R^5$, $R^6$, $R^7$, and $R^8$. These primary ring substituents optionally form additional fused rings having secondary ring substituents, as described below. Alternatively, the ring substituents are simple substituents such as H, halogen, or CN. Other allowed primary ring substituents are alkyl, perfluoroalkyl, or alkoxy having 1–6 carbon atoms; carboxy (—COOH), carboxyalkyl, carboxyalkoxy, carboxyalkylamino, or carboxylalkylthio each having 2–7 carbons. Any carboxy or carboxy substituted substituent is optionally further substituted by a 1-(acyloxy)alkyl ester having 2–7 carbons. Other pyridyl ring substituents are optionally amino, salt of amino (where the counterion is a halide, sulfate, substituted sulfonate, phosphate, perchlorate, tetrafluoroborate, tetraphenylboride, or anion of an aromatic or aliphatic carboxylic acid), alkylamino or dialkylamino, where each alkyl group has 1–6 carbons. Yet other ring substituents are sulfonic acid (—$SO_3H$), or salt of sulfonic acid (—$SO_3^-Z^+$, where Z is an alkali metal cation). Still other ring substituents are optionally aryl or heteroaryl. The primary ring substituents on the pyridyl rings are also optionally the attachment point for the remainder of the indicator —L—$F_L$.

Ring substituents are typically used to modify the solubility of the indicator, or alter the electronic environment of the metal ion-binding moiety. Alternatively, a ring substituent is used as a reactive site to further modify the indicator or to attach the indicator to a carrier or substrate. Typically, where the ion-binding moiety does not possess additional fused rings, two or fewer pyridyl ring substituents are non-hydrogen.

Ring substituents that are 1-(acyloxy)alkyl esters of carboxy are readily hydrolyzable esters that confer solubility or cell membrane permeability to the indicator, but which are readily cleaved by intracellular esterases. Typically the 1-(acyloxy)alkyl ester is an acetoxymethyl ($CH_3CO_2CH_2$—)ester.

Additional selected ring substituents are utilized to alter the solubility of the resulting indicator in either aqueous or organic solvents. Typically, the substitution of alkyl, alkoxy, perfluoroalkyl, CN, amino, alkylamino, dialkylamino, 1-(acyloxy)alkyl ester of carboxy, aryl or heteroaryl onto the metal ion-binding moiety results in an indicator conjugate that is more soluble in non-polar solvents. Alternatively, substitution is by a WATER SOLUBILIZING GROUP, i.e. a sulfonic acid, salt of sulfonic acid, salt of amine, carboxy, carboxyalkyl, carboxyalkoxy, carboxyalkylamino, or carboxyalkylthio or other substituent that results in an indicator conjugate that is more soluble in aqueous solution. Similarly, careful selection of the identity of L—$F_L$ is also used to modify the solubility of the final indicator with those indicators containing charged or ionizable groups usually enhancing water solubility.

An aryl substituent, as used herein, is a six-membered aromatic ring, attached by a single covalent bond, which is typically phenyl or phenyl substituted one or more times by a water-solubilizing group, but encompasses simple variations such as naphthyls and substituted naphthyls. Heteroaryl, as used herein, is an aromatic group that contains at least one heteroatom (a non-carbon atom forming the ring structure). A heteroaryl substituent is optionally a 5- or 6-membered ring, and is a single ring structure or a fused 2- or 3-ring structure. A heteroaryl substituent optionally contains one or more heteroatoms, e.g. pyrrolyl, pyridyl, thienyl, or furanyl (single ring, single heteroatom), or oxazolyl, isoxazolyl, oxadiazolyl, or imidazolyl (single ring, multiple heteroatoms), or benzoxazolyl, benzothiazolyl, or benzimidazolyl, (multi-ring, multiple heteroatoms), or quinolyl, benzofuranyl or indolyl (multi-ring, single heteroatom). Preferred heteroaryl substituents are 2-pyridyl or 2-quinolyl. Aryl and heteroaryl substituents are typically used to modify the spectral properties, affinity, selectivity, solubility or reactivity of the metal complex, or any combination of these factors. Both aryl and heteroaryl substituents are independently and optionally substituted by halogen; sulfonic acid or salt of sulfonic acid; alkyl, perfluoroalkyl or alkoxy (each having 1–6 carbons); or carboxy, carboxyalkyl, carboxyalkoxy, carboxyalkylamino, or carboxyalkylthio (having 2–7 carbons) (where any carboxy or carboxy substituted substituent is optionally further substituted by a 1-(acyloxy)alkyl ester having 2–7 carbons). Typically, the metal-ion binding moiety has no more than two aryl or heteroaryl substituents, that are usually attached at $R^1$ and/or $R^8$.

In addition to the above substituents, each pyridyl ring of the metal ion-binding moiety is optionally substituted by an additional fused aromatic ring. Any two adjacent pyridyl ring substituents taken in combination are optionally an additional fused aromatic ring; for example, $R^1$ and $R^2$ taken in combination, or $R^5$ and $R^6$ taken in combination. There are no more than two additional fused aromatic rings on the metal ion-binding moiety, one on each pyridyl ring. Metal ion-binding moieties that possess two additional fused aromatic rings may be symmetrically or unsymmetrically substituted. The fused aromatic ring substituents are independently and optionally substituted by halogen; sulfonic acid or salt of sulfonic acid; cyano; alkyl, perfluoroalkyl or alkoxy (each having 1–6 carbons); amino; alkylamino (having 1–6 carbons); dialkylamino (having 2–12 carbons); carboxy; or carboxyalkyl, carboxyalkoxy, carboxyalkylamino, or carboxyalkylthio (each having 2–7 carbons) (where any carboxy or carboxy substituted substituent is optionally further substituted by a 1-(acyloxy) alkyl ester having 2–7 carbons). Selected (but not exclusive) examples of metal ion-binding moieties having additional fused rings are shown below.

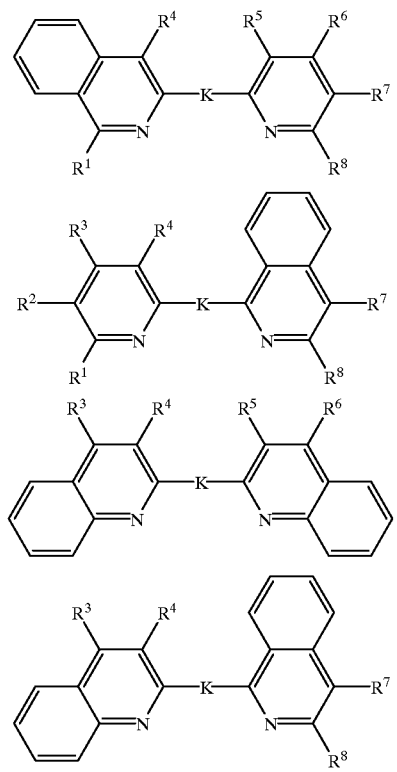

The aryl, heteroaryl, and additional fused ring substituents may serve as attachment points for —L—$F_L$.

In one embodiment of the invention, K is a single covalent bond, such that the metal ion-binding moiety is a bipyridyl-based chelator. Metal ion-binding moieties that are bipyridyls have the general structure:

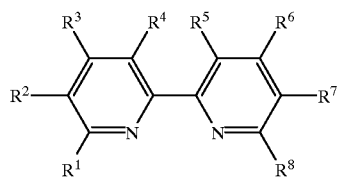

Typically, one of $R^1$–$R^8$ serves as the point of attachment for —L—$F_L$, and the remaining primary ring substituents are either a second —L—$F_L$, a WATER SOLUBILIZING GROUP, or are hydrogen.

In another embodiment of the invention, K is a formal single bond, and $R^4$ and $R^5$ when taken in combination are —$CR^9$=$CR^{10}$—, such that the moiety is an aromatic phenanthroline-based chelator having the general formula:

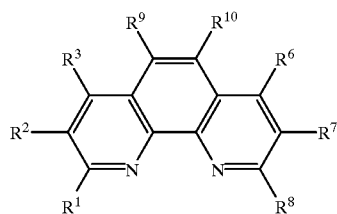

The phenanthroline substituents $R^9$ and $R^{10}$ are independently H; alkyl, perfluoroalkyl, or alkoxy having 1–6 carbon atoms; a sulfonic acid, a salt of sulfonic acid; an amino, alkylamino or dialkylamino, where each alkyl group has 1–6 carbons; a carboxy; or carboxyalkyl, carboxyalkoxy, carboxyalkylamino or carboxyalkylthio having 2–7 carbons (where any carboxy or carboxy substituted substituent is optionally further substituted by a 1-(acyloxy)alkyl ester having 2–7 carbons); an aryl or heteroaryl; halogen; or CN. The phenanthroline substituents $R^9$ and $R^{10}$ are optionally the attachment point for the remainder of the indicator, —L—$F_L$. Typically, one of $R^9$ and $R^{10}$ serves as the attachment point for —L—$F_L$ and all other ring substituents are hydrogen, phenyl or phenyl substituted by a WATER SOLUBILIZING GROUP.

When the metal ion-binding moiety is a phenanthroline-based chelator, adjacent pyridyl ring substituents are optionally combined to form additional fused aromatic rings, excepting that $R^4$ and $R^5$ are no longer available to form additional fused rings with $R^3$ and $R^6$, respectively. Additional fused aromatic rings are therefore only available using combinations of $R^1$, $R^2$, $R^3$, $R^6$, $R^7$ and $R^8$. Typically the phenanthroline-based indicator does not contain additional fused rings.

In another embodiment of the invention, K is —$(CR^{11}_2)_a$—$X_b$—$(CR^{12}_2)_c$—, such that the metal ion-binding moiety is a bis-pyridyl-based chelator. In this embodiment, a, b and c are each 0 or 1, excepting that when b=1, a+c must equal 0 or 2. Selected examples of bis-pyridyl-based chelators are shown below.

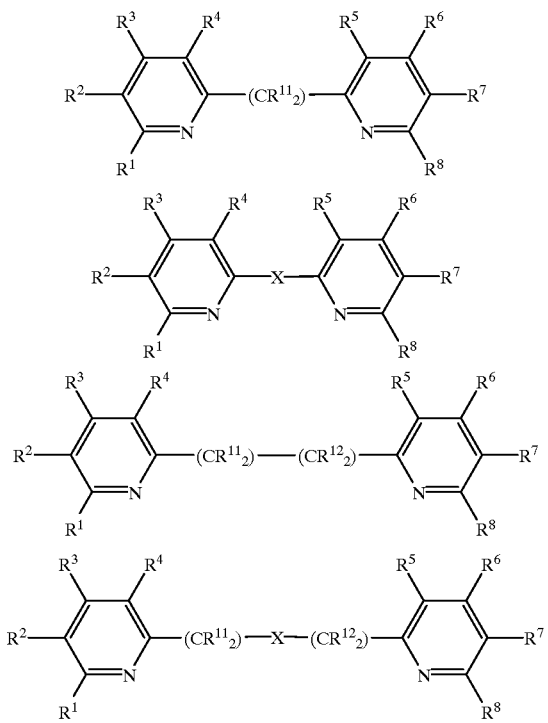

Each $R^{11}$ and $R^{12}$ is optionally and independently H or alkyl having 1–6 carbon atoms. The substituents $R^{11}$ and $R^{12}$ are also optionally the attachment point for the remainder of the indicator, —L—$F_L$ or positions for attachment of WATER SOLUBILIZING GROUPS. Typically, each $R^{11}$ and $R^{12}$ is hydrogen.

The element X is optionally O or S, yielding an ether or thioether bridge, respectively. Alternatively, X is $NR^{13}$, where $R^{13}$ is H, $C_1$–$C_6$ alkyl, or $R^{13}$ serves as the attachment point for —L—$F_L$. Alternatively, $R^{13}$ is phenyl that is optionally further substituted by alkyl, perfluoroalkyl, or alkoxy having 1–6 carbon atoms; sulfonic acid, salt of sulfonic acid; $NO_2$; amino, alkylamino or dialkylamino, where each alkyl group has 1–6 carbons; carboxy; carboxyalkyl, carboxyalkoxy, carboxyalkylamino or carboxyalkylthio having 2–7 carbons (where any carboxy or carboxy substituted substituent is optionally further substituted by a 1-(acyloxy)alkyl ester having 2–7 carbons); halogen, or CN. In yet another embodiment, X is —$CR^{14}R^{15}$—, yielding a trimethylene bridge, where $R^{14}$ and $R^{15}$ are independently H or alkyl having 1–6 carbons. Additionally, either of $R^{14}$ and $R^{15}$ optionally serves as an attachment point for —L—$F_L$. Typically, K is —$CR^{11}_2$—$NR^{13}$—$CR^{12}_2$—, and $R^{13}$ is phenyl or substituted phenyl. Preferably $R^{13}$ is phenyl or substituted phenyl, and —L—$F_L$ is attached to $R^{13}$ at the ring position para to the nitrogen atom, as shown in the structure:

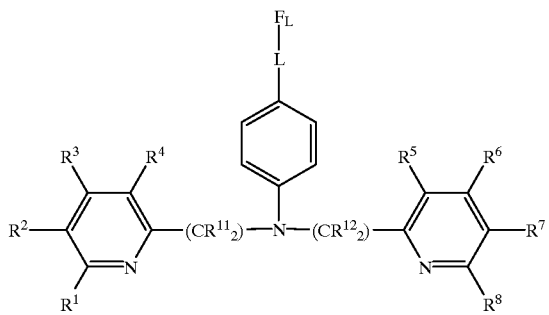

therefor.

In an alternate embodiment of the invention, K is a substituted 2,6-pyridyl, to yield all indicator having a terpyridyl-based complexing group, according to the following structure:

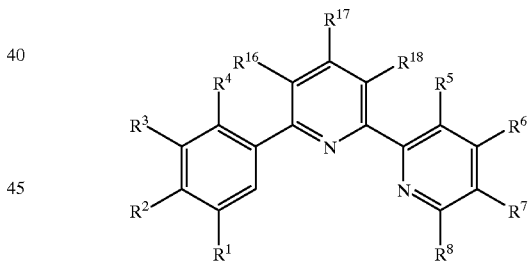

In this embodiment, the substituents $R^{16}$, $R^{17}$, and $R^{18}$ are independently H; alkyl, perfluoroalkyl, or alkoxy having 1–6 carbon atoms; sulfonic acid, salt of sulfonic acid; amino, alkylamino or dialkylamino, where each alkyl group has 1–6 carbons; carboxy; or carboxyalkyl, carboxyalkoxy, carboxyalkylamino, or carboxyalkylthio having 2–7 carbons (where any carboxy or carboxy substituted substituent is optionally further substituted by a 1-(acyloxy)alkyl ester having 2–7 carbons); halogen, or CN. Alternatively, one or more of $R^{16}$, $R^{17}$, and $R^{18}$ serves as the attachment point for —L—$F_L$. Typically $R^{16}$, $R^{17}$, and $R^{18}$ are hydrogen or —L—F. Preferably $R^{16}$ and $R^{18}$ are hydrogen and $R^{17}$ is —L—$F_L$.

For all embodiments, the metal ion-binding moiety has least one substituent that serves as an attachment point for an —L—$F_L$, but the metal ion-binding moiety has no more than two substituents that serve as attachment points for —L—$F_L$.

The Fluorophore

The fluorophore is a chemical moiety that, when conjugated to the metal ion-binding moiety, confers fluorescent properties on the resulting conjugate that are characteristic of the fluorophore. That is, a fluorophore is a chemical moiety that, when its conjugate is illuminated with visible, ultraviolet or infrared radiation at one wavelength, will emit radiation at a measurably different wavelength. Specific desirable fluorescence characteristics may include one or more of the following: a high extinction coefficient at the preferred wavelength of excitation, a high quantum yield, an optimal excitation or emission wavelength (preferably above 350 nm), or photostability. For example, fluorophores that are efficiently excited by inexpensive light sources such as tungsten bulbs, arc lamps or low power lasers are preferred for most analytical applications. Fluorophores useful for biological applications that can be excited and detected at visible wavelengths (350–700 nm) are preferred, with those excitable by the argon laser at 488 nm or 514 nm or those can be excited beyond 600 nm the most preferred. A broad variety of fluorophores are useful for practicing the instant invention.

Any fluorophore that gives a detectable response (as defined below) to the target metal when conjugated to the appropriate metal-binding moiety is suitable for practice of this invention. A wide variety of fluorophore conjugates provide a suitable response to a wide variety of metals. We provide, herein, procedures for testing the response of any possible instant fluorophore conjugate to any soluble metal, including testing for the lack of effect and lack of interference by non-target metals. Preferably, however, the fluorophore is chosen from those fluorophores that are known to have relatively high detectability. The factors that affect detectability of fluorescence in solution are well known and well documented in the literature (Haugland, MOLECULAR PROBES HANDBOOK OF FLUORESCENT PROBES AND RESEARCH CHEMICALS, (1992)) and include having strong absorbance, high quantum yields in the solvent used for fluorescence detection and photolytic stability. Other preferred properties that may affect the selection of a fluorophores include the emission and excitation wavelengths of the fluorophore, chemical stability, ease of synthesis, availability of suitable reactive forms for conjugation to the metal-binding moiety, freedom from nonspecific quenching by ions or other agents that may be present in the sample, and a molecular weight below 1000 g/mole. Among the most suitable fluorophores are those derived from a fluorescent dye chosen from the group consisting of xanthenes, such as fluoresceins, benzofluoresceins (U.S. Pat. No. 4,945,171 to Haugland et al., (1990)), naphthofluoresceins, eosins, erythrosins, rosamines, rhodamines (e.g., tetramethylrhodamine, sulforhodamines such as TEXAS RED dye), or rhodols (U.S. Pat. No. 5,227,487 to Haugland et al. (1993)). Additional useful fluorophores include benzimidazoles, phenoxazines (e.g., resorufin, nile blue), ethidiums, propidiums, anthracyclines, mithramycins, acridines, actinomycins, styryl dyes, carbocyanines, merocyanines, coumarins (e.g. 7-amino-4-methylcoumarins), pyrenes, chrysenes, stilbenes, carbazines, porphyrins, anthracenes, naphthalenes (e.g. dansyl, 5-dimethylamino-1-naphthalenesulfonyl), salicylic acids, anthranilic acids, benz-2-oxa-1,3-diazoles (also known as benzofurazans) (e.g. 4-amino-7-nitrobenz-2-oxa-1,3-diazole), fluorescamine, dipyrromethene boron difluorides (U.S. Pat. No. 4,774,339 to Haugland et al. (1988); and U.S. Pat. No. 5,274,113 to Kang et al. (1993)), dibenzopyrromethene boron difluorides (U.S. Pat. No. 5,433,896 to Kang et al. (1995)).

A preferred class of fluorophores is those that have long wavelength spectra, high absorbance and good quantum yields. Examples of these fluorophores are fluoresceins, rhodols, rosamines, rhodamines, carbocyanines, merocyanines, styryl dyes and porphyrins. More preferred fluorophores are fluoresceins, rhodamines, rosamines and rhodols, particularly those that additionally confer water-solubilizing properties on their conjugates with metal binding moieties. These dyes also appear to be particularly susceptible to yielding detectable optical changes on metal binding to their conjugates. In addition, a variety of fluorophores can be made more water-soluble by the substitution of one or more WATER SOLUBILIZING GROUPS, including but not limited to sulfonic acids, alkali metal salts of sulfonic acids, carboxy groups, alcohols and ammonium groups.

A second preferred class of fluorophores is those that absorb maximally at wavelengths greater than 360 nm, preferably greater than 400 nm. Typically, the fluorophore $F_L$ is excitable at wavelengths greater than 450 nm and possesses an emission peak beyond 500 nm. Preferred fluorophores have extinction coefficients exceeding 20,000 $cm^{-1}m^{-1}$, more preferably greater than 50,000 $cm^{-1}m^{-1}$, and yet more preferably greater than 70,000 $cm^{-1}m^{-1}$.

It has been postulated that a significant factor in making the instant indicators exhibit a fluorescence response upon binding a metal ion is the nature of the electronic interaction between the excited state of the fluorophore and the ion-binding moiety, and the degree to which that interaction is dependent upon the complexation of a metal ion. This effect, which has been termed "Photoinduced Electron Transfer" (PET) (see Bissel, et al., CHEM. SOC. REV. 187 (1992)), may be the major factor that explains the response of some of the instant indicators to certain metals. The preferred effect of an indicator whose response is based on PET is a quenching of fluorescence in the metal free conjugate and a loss of this quenching on metal binding. This results in a net increase in fluorescence on metal binding. Preferred fluorophores in this case are those that facilitate PET by being acceptors for the electron density associated with the metal-complexing moieties when in their excited states. The preferred target metals in this case are those that result in the largest fluorescence enhancements. Selection of preferred fluorophores can easily be made based on testing the fluorescence properties in the presence and absence of the target ion as provided for in Examples 10 and 11. Possible implication of a strong PET effect on the conjugate fluorescence can be inferred by comparing the fluoresence quantum yield of the metal-free conjugate with that of a structurally similar dye that is not attached to the metal-complexing moiety.

Alternatively, preferred fluorophores are those whose indicator conjugates are highly quenched upon binding of the metal to the metal-binding moiety. In this case, the preferred fluorophores are those whose fluorescence is not significantly quenched on conjugation to the metal-binding moiety, as determined by comparing the fluorescence of the indicator conjugate to that of a structurally similar dye that is not conjugated to the metal-binding moiety. In this case, quenching has usually been associated with a heavy atom effect, the effect of unpaired electron spins of the metal on intersystem crossing of the fluorophore, or to an excited state energy transfer of the dye to the metal, all of which result in net fluorescence quenching. The preferred metals for these indicator conjugates are those that result in a high degree of quenching of the dye conjugate's fluorescence. These are usually those metals that are paramagnetic or are themselves colored.

The Covalent Linkage

The covalent linkage L attaches the metal ion-binding moiety to the fluorophore to form the desired indicator. L is optionally a single bond or a linkage that is 9 or fewer non-hydrogen atoms in length. Typically L is a single bond, an alkyl linkage (—$(CH_2)_n$—, where n=1–6); a phenylene linkage (—$C_6H_4$—) or an ether, thioether, amine, sulfonamide, carboxamide, urea, thiourea, or aminotriazine linkage that is 9 or fewer non-hydrogen atoms in length or L is a combination of an alkyl or phenylene linkage and one or more of these functional groups. Preferably L is a single bond, a short alkyl linkage, a phenylene linkage, an amide, thiourea or sulfonamide or a combination of alkyl or phenylene linkages with an amide, thiourea or sulfonamide. It has been observed that a covalent linkage that is 9 or fewer atoms in length will yield an indicator having sufficient electronic communication between the ion-binding moiety and the fluorophore to give a detectable fluorescence response upon binding. However, it is possible that a covalent linkage that is greater than 9 non-hydrogen atoms in length will still produce a useful detectable fluorescence response upon binding a metal ion. More preferably, L contains a total length of 0 to 4 non-hydrogen atoms.

The specific nature of the covalent linkage L is a result of the method of conjugation used to attach the metal ion-binding moiety and the fluorophore to each other. Typically, the conjugates of the present invention are prepared by reaction of a metal binding chelator that has a suitable first reactive functional group with a fluorophore that possesses a second complementary reactive functional group. By second complementary reactive functional group is meant a functional group that will react, either spontaneously or in the presence of additional reagents, with the first reactive functional group present on the metal binding chelator. Numerous suitable pairs of reactive functional groups, and the type of linkages that result from their reaction, are known. Selected example of such functional groups and linkages are shown in Table 1.

TABLE 1

Examples of some routes to useful covalent linkages

| FIRST FUNCTIONAL GROUP (attached to metal ion-binding precursor) | SECOND FUNCTIONAL GROUP (attached to fluorophore precursor) | TO YIELD: (covalent linkage L) |
|---|---|---|
| alcohols/phenols | alkyl halides | ethers |
| haloacetamides | thiols | thioethers |
| maleimides | thiols | thioethers |
| alkyl halides | thiols | thioethers |
| alkyl sulfonates | thiols | thioethers |
| alkyl halides | alcohols/phenols | ethers |
| alkyl sulfonates | alcohols/pheriols | ethers |
| thiols | sulfonate esters | thioethers |
| thiols | haloacetamides | thioethers |
| thiols | maleimides | thioethers |
| thiols | epoxides | thioethers |
| amines/anilines | sulfonyl halides | sulfonamides |
| amines/anilines | carboxylic acids | carboxamides |
| amines/anilines | anhydrides | carboxamides |
| amines/anilines | activated esters* | carboxamides |
| amines/anilines | alkyl halides | alkyl amines |
| amines/anilines | isocyanates | ureas |
| amines/anilines | isothiocyanates | thioureas |
| amines/anilines | chlorotriazines | aminotriazines |
| amines/anilines | sulfonate esters | alkyl amines |
| carboxylic acids | amines/anilines | carboxamides |
| anhydrides | amines/anilines | carboxamides |
| activated esters* | amines/anilines | carboxamides |
| chlorotriazines | amines/anilines | aminotriazines |

TABLE 1-continued

Examples of some routes to useful covalent linkages

| FIRST FUNCTIONAL GROUP (attached to metal ion-binding precursor) | SECOND FUNCTIONAL GROUP (attached to fluorophore precursor) | TO YIELD: (covalent linkage L) |
|---|---|---|
| isocyanates | amines/anilines | ureas |
| isothiocyanates | amines/anilines | thioureas |

*Activated esters, as understood in the art, generally have the formula —COΩ, where Ω is a good leaving group (e.g. oxysuccinimidyl (—$OC_4H_4O_2$), -1-oxybenzotriazolyl(—$OC_6H_4N_3$); or a phenoxy group or phenoxy substituted one or more times by electron withdrawing substituents such as nitro, fluoro, chloro, cyano, or trifluoromethyl, or combinations thereof, used to form activated phenyl esters; or a carboxylic acid activated by a carbodiimide to form an anhydride or mixed anhydride —$OCOR^a$ or —$OCNR^aNHR^b$, where $R^a$ and $R^b$, which may be the same or different, are $C_1$–$C_6$ alkyl, $C_1$–$C_6$ perfluoroalkyl, or $C_1$–$C_6$ alkoxy; or cyclohexyl, 3-dimethylaminopropyl, or N-morpholinoethyl).

Solubility

Preferred indicators arc those that are sufficiently water soluble such that they are useful for assays conducted in aqueous- or partially-aqueous solution. For these indicators, either the metal ion-binding moiety, the fluorophore, the covalent linkage or a combination thereof is a moiety that confers sufficient water solubility on the conjugate to make the indicator-metal ion complex water soluble. Suitable substituents include carboxy, sulfonic acids, salts of sulfonic acids, salts of amines, alcohols, or water soluble polymers such as dextrans, proteins, polyethylene glycols. Sufficient solubility is the solubility needed to maintain a useful concentration of both metal-free and metal-bound forms of the indicator in the assay solution, typically a solubility of 0.1 $\mu$M to 10 $\mu$M.

Synthesis

The synthesis of heterocyclic nitrogen rings such as pyridines, bipyridyls, quinolines and phenanthrolines and methods for their chemical derivatization is extensively described in the scientific literature. The most useful nitrogen heterocycles for the present invention are those that contain reactive groups for coupling the heterocycle to the fluorophore, such as amines, thiols, hydroxy groups, carboxylic acids or sulfonic acids. Numerous such reactive heterocycles are commercially available or their syntheses have been described in the chemical literature. The same reactive groups can additionally be used to attach the indicator to polymers, to introduce solubilizing groups or to incorporate other permitted substituents. In the current invention, the preferred method of attaching a fluorophore to a heterocyclic nitrogen moiety is through an amide, thiourea or sulfonamide bond. This is accomplished, for example, by conjugating an amine-reactive fluorophores to an amine-containing heterocyclic nitrogen compound (as in Example 1). A wide range of amine-reactive fluorophores have been described, possessing a wide range of excitation and emission wavelengths. A variety of reactive fluorophores are either commercially available, or have been previously described (see, for example, Sets 4–7, MOLECULAR PROBES HANDBOOK OF FLUORESCENT PROBES AND RESEARCH CHEMICALS, Haugland, 1992 supra; U.S. Pat. No. 5,268,486 to Waggoner et al., (1993); U.S. Pat. No. 5,135,717 to Renzoni et al. (1992); International Publication No. WO 91/18006, by Arrhenius, published Nov. 28, 1991); and EPO Publication No. 0,277,139, B1 by Robinson, published Aug. 8, 1990). In this way, fluorescent conjugates with different colors of fluorescence are readily formed, based on the choice of reactive dye.

Alternatively, carboxylic acid- or sulfonic acid-containing heterocyclic nitrogen moieties are activated with a variety of reagents to give amine-reactive derivatives such as acid halides, symmetric or mixed anhydrides or succinimidyl esters, that are then used to couple the metal ion-binding heterocycle to an amine-containing fluorescent dye. Also alternatively, amines and carboxylic acids are covalently coupled using dehydrating agents, such as dicyclohexylcarbodiimide (DCC). One skilled in the art of conjugate chemistry would see that there are a wide variety of potential linkers that can be used to couple fluorophores to heterocyclic-nitrogen moieties.

Synthetic methods used to attach fluorophores to a variety of materials and biomolecules are well known in the art and have been reviewed (Brinkley, BIOCONJ. CHEM., 3, 2 (1992)). The general strategies for attachment of colorimetric and fluorescent dyes to substrates are readily adapted by one of ordinary skill to attach selected fluorophores to a selected metal ion-binding moiety.

The utility of the indicators of the present invention is optionally enhanced by their conjugation to a variety of polymers and biomolecules. Attachment of the indicator to a polymeric material or biomolecule can be used to impart ion-sensing properties on that substance and/or to solubilize, insolubilize or otherwise modify the properties of the indicator, the substance, or both. Typical examples of such substances include, but are not limited to, antibodies, amino acids, proteins, peptides, polypeptides, enzymes, enzyme substrates, lipids, phospholipids, hormones, lymphokines, metabolites, antigens, haptens, drugs, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatized nucleic acids (including deoxyribo- and ribonucleic acids), DNA and RNA fragments and derivatized fragments (including single and multi-stranded fragments), natural and synthetic drugs, receptors, virus particles, bacterial particles, virus components, biological cells, cellular components (including cellular membranes and organelles), natural and synthetic lipid vesicles, polymers, polymer particles, polymer membranes, conducting and non-conducting metals and non-metals and glass and plastic surfaces and particles.

Alternatively, the indicator is conjugated to a polymer film or a polymer microparticle, wherein the polymer is polyacrylamide. In this embodiment, the polymer microparticle is typically spherical or nearly spherical and the particle size is typically greater than 0.01 $\mu$m and less than 50 $\mu$m. In another embodiment, the indicator is conjugated to a dextran, a modified dextran or glass. Where the indicator is conjugated to a dextran, the dextran typically has a molecular weight greater than 1000 and less than 1,000,000. Where the polymer is a glass, it is optionally incorporated into an optical fiber or is coated on an optical fiber.

The desired indicator-conjugate is most easily prepared when the indicator is initially substituted by amino, or carboxylate or other readily reactive substituent as listed in Table 1. These substituents are readily converted to a reactive derivative that is then attached to polymers, lipids, members of specific binding pairs or other materials. The reactive substituent may be bound to either the metal ion-binding moiety or the fluorophore portion of the indicator or may be part of either K or L. The appropriate reactivities and procedures to prepare the reactive indicators and conjugates is completely described in U.S. Pat. No. 5,453,517, supra, incorporated by reference.

Method of Use

A specific indicator of the present invention is useful for the detection and/or quantification of a desired target ion, when the binding of the target ion in the metal ion-binding moiety of the indicator results in a detectable fluorescence response.

A detectable fluorescence response, as used herein, is a change in a fluorescence property of the indicator that is capable of being perceived, either by direct visual observation or instrumentally, and the presence or magnitude of which is a function of the presence of a target metal ion in the test sample. This change in a fluorescence property is a change in fluorescence quantum yield, fluorescence polarization, fluorescence lifetime, a shift in excitation or emission wavelength or a combination of these effects. The detectable change in a given spectral property is either an increase or a decrease. However, spectral changes that result in an enhancement of fluorescence intensity and/or a shift in the wavelength of fluorescence emission or excitation are preferred. The change in fluorescence on ion binding is due to conformational or electronic changes in the metal ion-binding chelator that may occur in either the excited or ground state of the dye, to changes in electron density at the binding site, to quenching of fluorescence by the bound target metal ion or to any combination of these or other effects.

A preferred indicator for a specific target ion is an indicator that shows at least a two-fold change in net fluorescence emission intensity (either higher or lower), or a 25% difference in fluorescence lifetime (either shorter or longer), preferably a five-fold or greater change in net fluorescence emission intensity or a 100% change in fluorescence lifetime in response to the target ion. Alternatively, the ion that shifts the excitation or emission wavelength of the indicator at least 10 nm (either to shorter or longer wavelength), preferably 25 nm or greater is preferred.

The response of an individual indicator to a specific metal ion is dependent on the properties of both the bound and unbound indicator, the relative electron densities of the dye and metal binding site and the ability of metal ions to quench fluorescence emission when in close proximity to a fluorophore (heavy atom quenching). For selected embodiments of the invention, the indicator is highly fluorescent in the absence of the target metal ions and shows a decrease in fluorescence and fluorescence lifetime upon binding the target metal ion. In another embodiment of the invention, the indicator is nonfluorescent or has low fluorescence in target ion-free solution and exhibits an increase in fluorescence intensity or fluorescence lifetime upon target metal ion binding. In yet another embodiment of the invention, the fluorescence intensity remains approximately the same but there is a shift in the excitation or emission spectrum, or both, upon metal ion binding.

In selecting the appropriate fluorescent indicator for a particular target ion and/or concentration range, the binding affinities for heterocyclic nitrogen-based chelators are first estimated from literature values (e.g., Martel et al., supra) or determined by standard methods. A nitrogen-based chelator, or substituted nitrogen-based chelator is then selected that possesses or would be expected to possess an appropriate binding affinity for the desired target ion in the expected concentration range. A fluorescent conjugate of the selected nitrogen-based chelator (or a structurally similar metal ion binding site) is then prepared and evaluated for the fluorescence response upon binding the target ion. For example, it is known that phenanthroline and bathophenanthroline-based chelators possess very high affinities (in the nanomolar range) for $Fe^{2+}$, $Cu^{2+}$, $Cu^+$, $Hg^{2+}$ and other divalent cations. Similarly, bipyridyl-based chelators typically bind with high affinity to $Ni^{2+}$, $Zn^{2+}$, $Cu^{2+}$ and biquinoline-based chelators bind with high affinity to $Cu^+$, $Cu^{2+}$ and $Zn^{2+}$. If, for instance an indicator for $Cu^{2+}$ was desired, a fluorescent conjugate of a phenanthroline, bathophenanthroline, bipyridyl or biquinoline should be prepared for evaluation of fluorescence response. However, if an indicator for $Fe^{2+}$ was desired, a fluorescent conjugate of phenanthroline or bathophenanthroline should be prepared. Pyridyl-based indicators, which includes quinolines and phenanthrolines are recognized to complex with varying affinities with almost all polyvalent metals but they have good rejection of most monovalent metals, $Ca^{2+}$ and $Mg^{2+}$. Nitrogen-heterocycles that complex metals with the highest affinity are most effective in detecting the target metals when the metal is expected to be at ppm or ppb concentrations.

Upon selecting a target ion, the optimal indicator for that target ion is determined in the selected medium prior to performing an assay. The medium is typically an aqueous or partially aqueous solution, although the test may be conducted in partially aqueous or nonaqueous homogeneous solution if the complex is sufficiently soluble. The test may also be conducted using an indicator immobilized onto a surface such as glass or paper provided that suitable equipment for qualitative or quantitative determination of the response is available. To determine the metal sensitivities for an indicator of the present invention in homogeneous solution, aliquots of a dilute solution (usually 0.1 to 5 $\mu$M) of a selected indicator are prepared in pure water buffered to pH 7.0 with a volume appropriate to the apparatus used to detect the indicator's fluorescence response. Typically, the concentration of the indicator is chosen so as to yield a sufficient signal in the apparatus used for the detection of the fluorescence response. Depending on the binding affinity of between the metal and the indicator and the solubility of the metal in the medium, aliquots of selected metal-ion solutions (including the desired target ion, and any other ions likely to be present in the test sample) are added to the samples of the dye solution to bring the final metal ion concentration to between 5 $\mu$M and 1 mM, more typically 5 and 100 $\mu$M, preferably between 10 and 25 $\mu$M. The fluorescence properties of the samples are then compared with those of a standard "metal ion-free" buffer containing a strongly binding, nonfluorescent metal chelator for the target metal at high concentrations and similar pH (e.g. 10 mM $K_2$EGTA at pH 7.2). The fluorescence response of the indicator is recorded in the presence of each selected metal ion. For example, if the fluorescence responses have been detected and recorded using a fluorimeter, the spectral responses can be plotted together. It is not uncommon for the fluorescence response to be enhanced or otherwise altered by addition of a water-miscible organic solvent to the assay mixture. Indicators that yield a detectable change in excitation wavelengths, emission wavelengths, fluorescence lifetimes or other measurable spectral property over the concentration range of interest for the desired target ion are useful for the determination of the presence of that ion.

Alternatively, in the case of an indicator whose metal complex is to be detected in a water-immiscible organic medium but whose target metal ion is dissolved in an aqueous medium, sensitivity and selectivity of a potential target metal indicator is tested by mixing the sample with a likely molar excess of the indicator in a mixture of water and a partially water-immiscible solvent such as a lower alkyl ester or ether, a ketone with about 5–10 carbon atoms, a lower alcohol, or a hydrocarbon or partially chlorinated hydrocarbon, provided that the extracted metal complex is sufficiently soluble in the organic layer and that greater than about 75% of the metal, preferably greater than 90% and, more preferably, greater than 97% of the target ion is extracted into the organic layer by the indicator complex. In this case, the metal complex is usually detected by fluorometry or by visual inspection following excitation in the organic layer with or without separation from the aqueous layer. The preferred indicators in this case are those than do not contain water solubilizing groups.

Preferred embodiments of the indicators of the invention possess a high selectivity, that is, they show a high rejection of non-target ions. This ability to detect a non-target ion can be tested by a comparable titration of the indicator with that ion. The selectivity of a chosen indicator is often improved by the addition of a second metal complexing agent that selectively binds an otherwise interfering non-target ion with a higher affinity than the chosen indicator. This second metal chelator (for example 2,3-dimercaptosuccinic acid or cyanide) can mask the interference by the non-target ion (for example $Hg^{2+}$). Removal of interference by certain ions can also be removed in some cases by precipitation of the interfering ion such as by addition of sulfide or carbonate, or by the oxidation or reduction of the interfering ion either chemically or electrochemically. High selectivity of the indicator is not required when the target ions are separated into fractions such as by ion chromatography, ion exchange chromatography or electrophoretic techniques. In this case the fluorescent indicator is added to the sample following separation, much in the same way as with other postcolumn detection reagents. High selectivity is also not required in samples where the potentially interfering ions are known to be absent. Separation techniques that involve selective extraction from the aqueous solution also improve the selectivity over interfering ions. Either the target metal or the interfering ion(s) can be extracted into the organic layer. Furthermore, reagents such as ethylenediaminetetraacetic acid (EDTA) are sometimes added to the aqueous layer to facilitate selective extraction of the target metal into the organic layer while retaining the interfering ion(s) in the aqueous layer. Depending on which procedure is more convenient and the sensitivity required, detection of the target ion can be made either in the organic solution or following removal of the organic solvent.

Upon evaluation of the response of the selected indicator, if the fluorescence response to the desired target ion does not fall within the required parameters for the assay being evaluated, a conjugate of a different metal ion-binding moiety is prepared for evaluation. Alternatively, the binding affinity and fluorescence response of the initially selected indicator can be altered by modifying the electronic environment of either the fluorophore or the metal-ion-binding moiety with the substitution of appropriate electron-donating or electron-withdrawing substituents, by methods well known in the art. The careful selection of different fluorophores can also be used to "fine-tune" the electron density at the metal binding site.

Once an indicator has been prepared that is suitable for the desired target ion, the optimal concentration range of indicator response is determined by preparing aliquots of a dilute indicator solution as above and adding increasing amounts of the target ion. For example, if a 25 $\mu$M metal ion concentration gives a ten-fold increase in fluorescence emission intensity, the target ion is then tested at concentrations above and below this level to give an estimate of the concentrations of target metal ion over which the indicator is most sensitive (e.g. 1, 5, 10 and 50 $\mu$M target ion). Based on the results of this evaluation, a third test is run to determine the dissociation constant ($K_d$) of the indicator for the selected target ion(s).

To determine the $K_d$ for the ion-indicator complex, aliquots of a dilute indicator solution are prepared as described above, and the target metal ion is added to each so as to give a regular gradient of increasing concentration, from zero to the saturating concentration. For example, if an indicator that has an increase in emission intensity is used, the indicator/metal ion solutions are observed and the fluorescence intensity at the peak emission of the indicator is recorded for each ion concentration. This data is then plotted as the change in fluorescence intensity versus ion concentration using a double log plot to give the $K_d$ as the reciprocal log of the x-intercept (as in Example 10, and FIG. 2). The most useful range of analyte concentration for quantitative measurements is about one log unit above and below the dissociation constant of the ion-indicator complex. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects need to be taken into account when calibrating an indicator. For qualitative measurements, where it is only necessary to know that the concentration of the target metal ion exceeds a predetermined value, it is typically sufficient to add the diluted or undiluted sample to the indicator and to compare the resultant fluorescence with that of a standard.

The indicator is combined with a sample in a way that will facilitate determination of the presence of the target ion in the sample. The sample is typically an aqueous or aqueous miscible solution that is obtained directly from a liquid source, or is an aqueous suspension of a solid or semi-solid material, or is an aqueous wash from a solid or semi-solid material that is known or suspected to contain the target ion. The sample may also be from an acidic, basic, or other digestion of an organic or inorganic material. The oxidation state of metal ion may be changed from its original state in the sample such as by chemical or electrochemical reduction or oxidation. The test sample is typically obtained from an environmental source such as soil, water, or air. The test sample is optionally derived from an industrial source, such as taken from a waste stream, a water source, a supply line, or a production lot. Industrial sources also include fermentation media, such as from a biological reactor or food fermentation process. Industrial sources alternatively include chemical reactors and bioreactors. Alternatively, the test sample includes intracellular fluids such as in blood cells, cultured cells, muscle tissue, neurons and the like; extracellular fluids in areas immediately outside of cells; in vesicles; in vascular tissue of plants and animals; or in biological fluids such as blood, saliva, and urine. The sample is optionally clarified before use, such as by filtration or centrifugation. The metal ions may be concentrated or separated wholly, or in part, such as by chromatography, electrophoresis or selective extraction.

Test samples containing greater concentrations of metals can be diluted preceding the assay. Samples that may contain otherwise undetectable concentrations of the target ion may be concentrated before the assay, such as by evaporation, ion exchange chromatography, or selective extraction into organic solvents.

The indicator is added to the test sample as an aqueous indicator solution, a non-aqueous indicator solution, or immobilized on a solid or semi-solid support. In either case, the indicator concentration must be sufficient to generate a detectable fluorescent response in the presence of the target metal ion of interest.

In one embodiment of the invention, the indicators of the present invention are prepared for use by initially dissolving the indicator to prepare an aqueous or partially aqueous indicator solution. The indicator solution has an indicator concentration sufficient to generate a detectable fluorescent response in the presence of the target metal ion of interest.

Typically, for a given target ion, the resulting indicator solution has a concentration of 100 nm to 20 $\mu$M in water or aqueous buffer. More typically the indicator solution has a concentration of 1 $\mu$M to 10 $\mu$M, and preferably a concentration of 2 $\mu$M to 5 $\mu$M. Depending on the solubility properties, the conjugate is initially dissolved in a water-miscible solvent, such as methanol, DMF, dioxane or DMSO, then diluted into an aqueous solution to the desired concentration. Modifications that are designed to enhance permeability of the indicator through the membranes of living cells, such as acetoxymethyl esters and acetates, may require the indicator to be predissolved in an organic solvent such as dimethylsulfoxide (DMSO) before addition to a cell suspension, where the indicators then readily enter the cells. Intracellular enzymes cleave the esters to the more polar acids and phenols that are then well retained inside the cells.

In another embodiment of the invention, the indicator is present by virtue of being immobilized or adsorbed on a solid or semi-solid support. Alternatively, the indicator is present in a gel or other matrix. In this embodiment, contact between the test sample and the indicator optionally requires agitation of the test sample, additional time for the diffusion of target ions to the indicators, use of semi-permeable or ion-selective membranes to enhance selectivity or other considerations.

After addition of the indicator to the test sample, the sample is illuminated by a light source capable of exciting either the free indicator, the indicator-ion complex, or both. In those embodiments wherein binding the metal ion results in a loss of fluorescence, the observation of a loss of fluorescent signal from the free indicator serves as an indication that the target ion is present. Typically, the sample is excited by a light source capable of producing light at or near the wavelength of maximum absorption of the indicator complex, such as an ultraviolet or visible wavelength emission lamp, an arc lamp, a laser, or even sunlight or ordinary room light. Preferably the sample is excited with a wavelength within 20 nm of the maximum absorption of the indicator-ion complex. Although excitation by a source more appropriate to the maximum absorption band of the indicator-ion complex results in higher sensitivity, the equipment commonly available for excitation of fluorescent samples can be used to excite the indicators of the present invention.

Changes in the indicator's fluorescence properties (quantum yield, lifetime, polarization or wavelength) upon binding the target ion are detected qualitatively, or optionally quantitatively, by detection of the resultant light emission. The emission is detected by means that include visual inspection, CCD cameras, video cameras, photographic film, or the use of current instrumentation such as laser scanning devices, fluorometers, photodiodes, quantum counters, epifluorescence microscopes, scanning microscopes, flow cytometers, fluorescence microtiter plate readers, or by means for amplifying the signal such as photomultiplier tube. Indicators can be selected to have emission bands that match commercially available filter sets such as that for fluorescein or for detecting multiple fluorophores with several excitation and emission bands.

The step of observing is optionally made remotely by incorporation of the indicator as part of a fiber optic probe. In this embodiment of the invention, the indicator is covalently attached to the fiber optic probe material, typically glass or functionalized glass (e.g., aminopropyl glass) or the indicator is attached to the fiber optic probe via an intermediate polymer, such as polyacrylamide. The indicator solution may alternatively be incorporated non-covalently within a fiber optic probe, or separated from the sample by a semi-permeable membrane, as long as there is a means whereby the target metal ion can come into contact with the indicator solution.

The observation of a detectable change in the fluorescence properties of the indicator (detectable fluorescence response) is optionally used to simply identify the presence of the target ion in the test sample. Alternatively, the detectable fluorescence response is quantified and used to measure the concentration of the target ion in the test sample. Quantification is typically performed by comparison of the fluorescence response to a standard, or calibration, curve. The standard curve is generated according to methods known in the art using varying and known amounts of the target ion in standard solutions, or by comparison with a reference dye or dyed particle that has been standardized versus the target ion-indicator complex.

Figure 5:
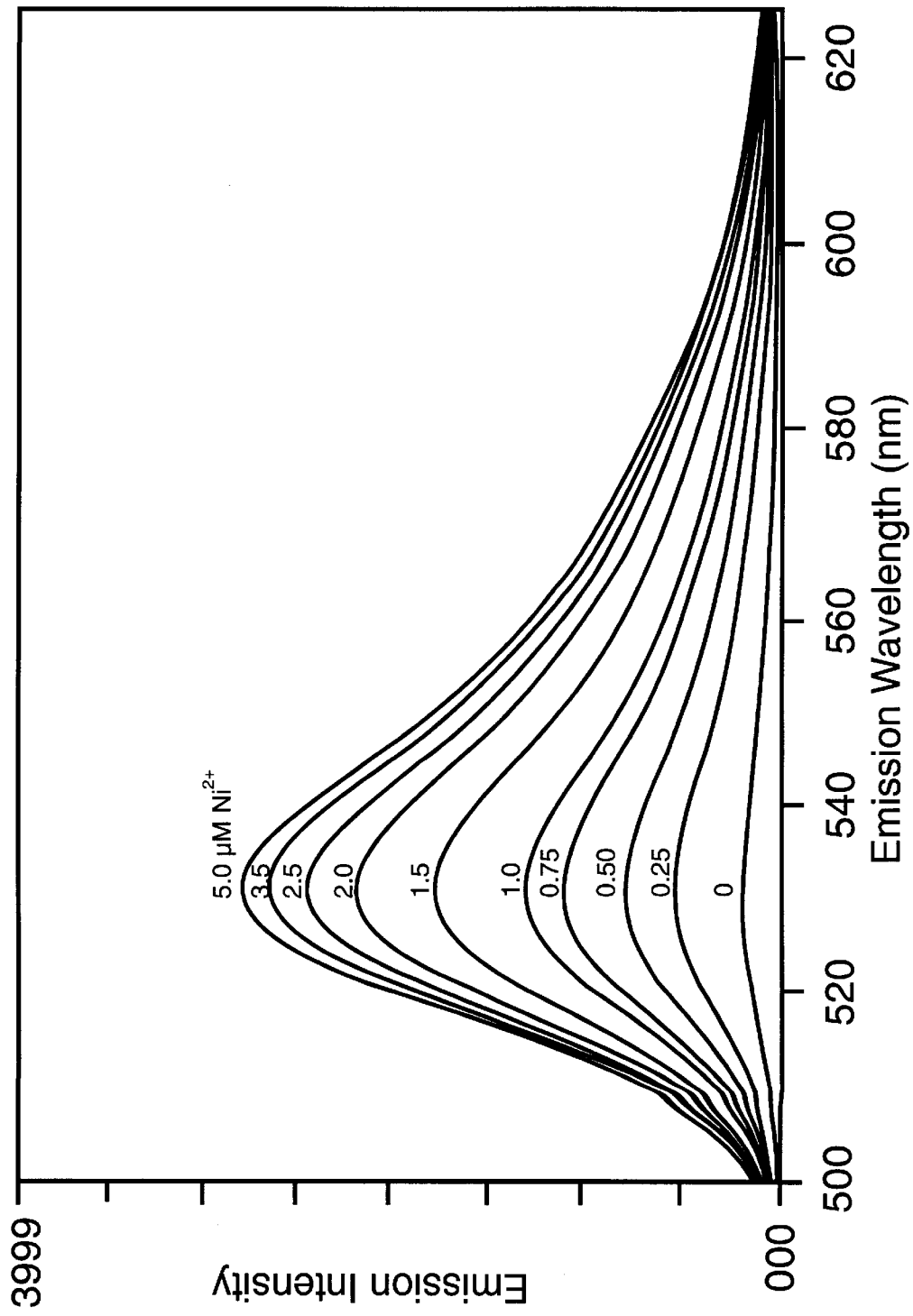
FIG. 5: The relative fluorescence emission intensity of a fluorescein bis-pyridyl conjugate in response to concentrations of $Ni^{2+}$ from 0 to 5 $\mu$M.

For some embodiments of the invention, different oxidation states of the same metal (e.g., $Cu^+/Cu^{2+}$, $Fe^{2+}/Fe^{3+}$, $Ce^{3+}/Ce^{4+}$, $Hg^+/Hg^{2+}$, etc.) are differentiated, due to detectably different fluorescence responses, or due to responses that are differentiable because they occur at different concentrations of the respective oxidation states (as in Example 11, FIG. 5). In the latter case, it is preferred that the relative affinities of the oxidation states differ by at least 10-fold, more preferably by greater than 100-fold. The different oxidation states of a given metal may exist simultaneously due to the presence of a chemical or biological oxidizing or reducing agent, or due to an externally applied electrical potential.

Indicators of the present invention are typically useful for the detection/quanitification of stable and soluble metal ions having an oxidation state of +1 to +4 and that are positively charged in solution. In particular, stable and soluble metal ions belonging to Groups 3–15 are potential target ions for the indicators of the present invention. Preferably, the target ion for the present indicators is selected from the group consisting of $Mn^{2+}$, $Fe^{2+}$, $Fe^{3+}$, $Co^{2+}$, $Ni^{2+}$, $Cu^{2+}$, $Cu^+$, $Zn^{2+}$, $Al^{3+}$, $Cd^{2+}$, $Ag^+$, $Au^+$, $Tl^+$, $Pd^{2+}$, $Hg^{2+}$, $Hg^+$, $Sn^{2+}$, $Pb^{2+}$, $Sr^{2+}$, $Ba^{2+}$, $Mo^{3+}$, $Ga^{3+}$, $In^{3+}$, $La^{3+}$, $Eu^{3+}$, $Tb^{3+}$, $Dy^{3+}$, $Ru^{3+}$, $Sc^{3+}$, $As^{3+}$, $Sb^{3+}$, $Cr^{3+}$, $Bi^{3+}$, $Ce^{3+}$, $Ce^{4+}$, $Pd^{2+}$, $Pt^{2+}$ and $Pt^{4+}$ ions. More preferably, the target ions of the instant indicators are transition elements or lanthanides in their oxidation states of +1 to +3. Even more preferably, they are selected from the group consisting of $Mn^{2+}$, $Fe^{2+}$, $Fe^{3+}$, $Ni^{2+}$, $Cu^{2+}$, $Cu^+$, $Zn^{2+}$, $Cd^{2+}$, $Ag^+$, $Au^+$, $Hg^{2+}$, $Pb^{2+}$, $Eu^{3+}$ and $Tb^{3+}$. Most preferably they are $Fe^{2+}$, $Fe^{3+}$, $Ni^{2+}$, $Cu^{2+}$, $Cu^+$, $Hg^{2+}$, or $Pb^{2+}$.

The examples below are given so as to illustrate the practice of this invention. They are not intended to limit or define the entire scope of this invention.

EXAMPLES

Example 1
Fluorescent Phenanthroline Indicators

The starting material, 5-amino-1,10-phenanthroline is treated with an amine-reactive fluorescent dye according to the general procedure that follows:

A solution of 195 mg (1.0 mmole) 5-amino-1,10-phenanthroline (Polysciences, Inc.) is prepared in 3 mL dry dimethylformamide that contains 202 to 303 mg (2.0 to 3.0 mmoles) triethylamine. The powdered, amine-reactive dye (1.2 mmoles) is added to the solution and the reaction is stirred until the 5-amino-1,10-phenanthroline mostly disappears, as monitored by silica gel thin layer chromatography (TLC) using 5:1 chloroform:methanol. The reaction mixture is then poured into 25 mL water, and the pH of the solution is adjusted to 4 to 5 using 6 M HCl. The resulting solid product is separated by filtration or centrifugation and washed well with water. Depending on the nature of the fluorescent dye used, the product is recrystallized (usually from methanol or isopropyl alcohol) or purified by either chromatography on silica gel or reverse phase chromatography on SEPHADEX LH-20 resin using 9:1 water:methanol or pH 8 water for elution. When purified by chromatography the appropriate fractions are collected, acidified when necessary and either evaporated or lyophilized. The final products are typically characterized by a combination of NMR, absorption spectroscopy, fluorescence spectroscopy and HPLC.

As a specific example, 1 mmole of 5-amino-1,10-phenanthroline is reacted with 1.2 mmole fluorescein-5-isothiocyanate in the presence of 3 mmoles triethylamine according to the method above. Following acid precipitation, the product is purified by dissolving it in dilute ammonia, chromatographing it by reverse phase chromatography using pH 8 KOH for elution, collecting the yellow-colored fractions, analyzing them by TLC, acidifying the solutions to pH 4, collecting the resulting precipitate, and drying it under high vacuum. The yield is approximately 440 mg (75%). The product is characterized by having an absorption maximum of 490 nm (in water at pH 8.0) with an extinction coefficient of 68,500 $cm^{-1}M^{-1}$.

Using similar synthetic methods, fluorescent conjugates of 5-amino-1,10-phenanthroline are prepared with the amine-reactive fluorescent dyes mixed anhydride of 5(6)-carboxytetramethylrhodamine with isobutyl chloroformate, LISSAMINE Rhodamine B sulfonyl chloride, TEXAS RED sulfonyl chloride dye, 1-pyrenesulfonyl chloride, 2-anthraceneisothiocyanate, 7-diethylamino-3-(4-isothiocyanatophenyl)-4-methylcoumarin, acridone-10-acetyl chloride, dansyl chloride, N-methylisatoic anhydride and 4,4-difluoro-4,7-dimethyl-4-bora-3a,4a-diaza-s-indacene-3-propionyl chloride.

Example 2
Fluorescent Substituted Phenanthroline Indicators

Bathophenanthroline disulfonic acid (Aldrich Chemical Company) is converted to the disulfonyl chloride by dissolving in phosphorous oxychloride at 50° C. for one hour. The reaction mixture is added to ice water then extracted into chloroform then evaporated to a solid. A solution of 4'-(aminomethyl)-fluorescein (390 mg, 1 mmole), is dissolved in a minimum volume of dimethylformamide and bathophenanthroline disulfonyl chloride (800 mg, 1.5 in mmole) is added. After standing overnight, the solution is evaporated to dryness and the crude product is purified on a SEPHADEX LH-20 resin column that is eluted with water adjusted to pH 8.5 with sodium hydroxide. The yellow product-containing fractions are separately evaporated and analyzed by HPLC. Those containing an approximately constant ratio of long wavelength absorption (490 nm) to UV absorption (330 nm) are combined and evaporated. The solids are rechromatographed on the same type of column to give 250 mg (30% yield) of the tetrasodium salt as an orange powder.

Example 3
Fluorescent Biquinolyl Indicators

Bicinchoninic acid (BCA) (0.7 g, 1.9 mmoles) is suspended in 20 mL methylene chloride. Triethylamine (0.5 mL, 3.8 mmoles) is added dropwise over five minutes. Isobutyl chloroformate (0.5 g, 4 mmoles) is dissolved in 10 mL methylene chloride and this is added to the solution of BCA over ten minutes at room temperature. The reaction is stirred for 12 hours, resulting in a colorless precipitate. Thin layer chromatographic analysis using silica gel and eluting with ethyl acetate shows a mixture of mono- and di-anhydride. The reaction mixture is diluted with ethyl acetate, filtered and evaporated to give a foam (0.6 g). This is dissolved in 15 mL DMF and 4'-(aminomethyl)-fluorescein, hydrochloride (1.1 g, 2.85 mmoles) is added in one portion. The reaction mixture is stirred at room temperature for three hours until thin layer chromatography in chloroform:methanol:acetic acid 89:10:1 shows complete conversion of the amine to two orange products. The solution is evaporated, suspended in water and the mixed products are precipitated with dilute HCl then separated by centrifugation. The pellet is resuspended in 5 mL water and the pH adjusted to 9 with 5% KOH. The crude products are separated by reverse phase chromatography to give two distinct bands. The mono- and di-substituted quinolines are characterized by the ratio of absorbance at 330 nm and 490 nm.

Using similar synthetic methods, bicinchoninic acid can be converted to a fluorescent indicator containing either one or two dyes by reaction with other fluorescent amines that include: LISSAMINE Rhodamine B sulfonyl ethylenediamine, N-(2-aminoethyl)-(2-(1,3,6-trisulfopyrenyl)oxy)acetamide, trisodium salt (the conjugate of CASCADE BLUE dye with ethylenediamine), 7-diethylamino-3-(4-aminophenyl)-4-methylcoumarin or 1-aminomethylpyrene.

In the case of bicinchoninic acids containing a single fluorophore, the remaining free carboxylic acid can be activated for coupling to either a second amine-containing dye or to an amine-containing polymer. Depending on the reactivity of the amine to which it is to be coupled, and the fluorophore already attached, the activation is mediated either by 1-dimethylaminopropyl-3-ethylcarbodiimide, hydrochloride (EDAC), disuccinimidyl carbonate or by isobutyl chloroformate plus triethylamine. For water soluble polymers, the adduct is separated from unconjugated indicator by dialysis or gel filtration. Conjugates of water insoluble polymers are separated from any free dye by washing with dilute base.

Example 4
Fluorescent Bipyridyl Indicators

Fluorescent bipyridyl indicators are prepared using synthetic methods that are entirely analogous to those described in Example 3, excepting that the starting material is a bipyridyl carboxylic acid such as 2,2'-bipyridine-4,4'-dicarboxylic acid (Aldrich Chemical Company).

Example 5
Fluorescent Terpyridyl Indicators

A key intermediate to preparation of certain terpyridyl indicators is a 4'-amino-2,2':6',2"-terpyridine, which can be prepared from 4'-chloro-2,2':6',2"-terpyridine (Aldrich Chemical Co). by reaction with p-aminobenzoic acid in the presence of CuO and potassium carbonate (ORG. SYNTH. 2, 15 (1943)). The benzoic acid is then treated with a reactive fluorophore using synthetic methods analogous to those described for preparing bicinchoninic acid derivatives in Example 3.

For example, the acid is first converted to the mixed isobutyl anhydride and then treated with 5-(aminomethyl)-fluorescein to give a green fluorescent indicator, or is treated with LISSAMINE rhodamine B sulfonylethylenediamine to give a red fluorescent indicator.

Example 6
bis-Pyridyl Indicators Substituted on the Bridge by an Aromatic Spacer A solution of 2-(tert-butoxycarbonyloximino)-2-phenyl acetonitrile (9.10 g, 37 mmoles) in 100 mL DMF is added dropwise to a stirring solution of p-phenylenediamine (20 g, 0.18 moles) in 400 mL DMF. The resulting reaction mixture is stirred at room temperature 14 hours. The reaction mixture is then diluted with 500 mL ethyl acetate and washed twice with 75 mL 5% HCl. The layers are separated, the pH of the aqueous layer is adjusted to 9 with concentrated ammonium hydroxide, and then extracted into 300 mL chloroform. The chloroform solution is then evaporated, and the resulting residue is recrystallized from ethyl acetate (5.1 g, 66% yield).

Figure 6:
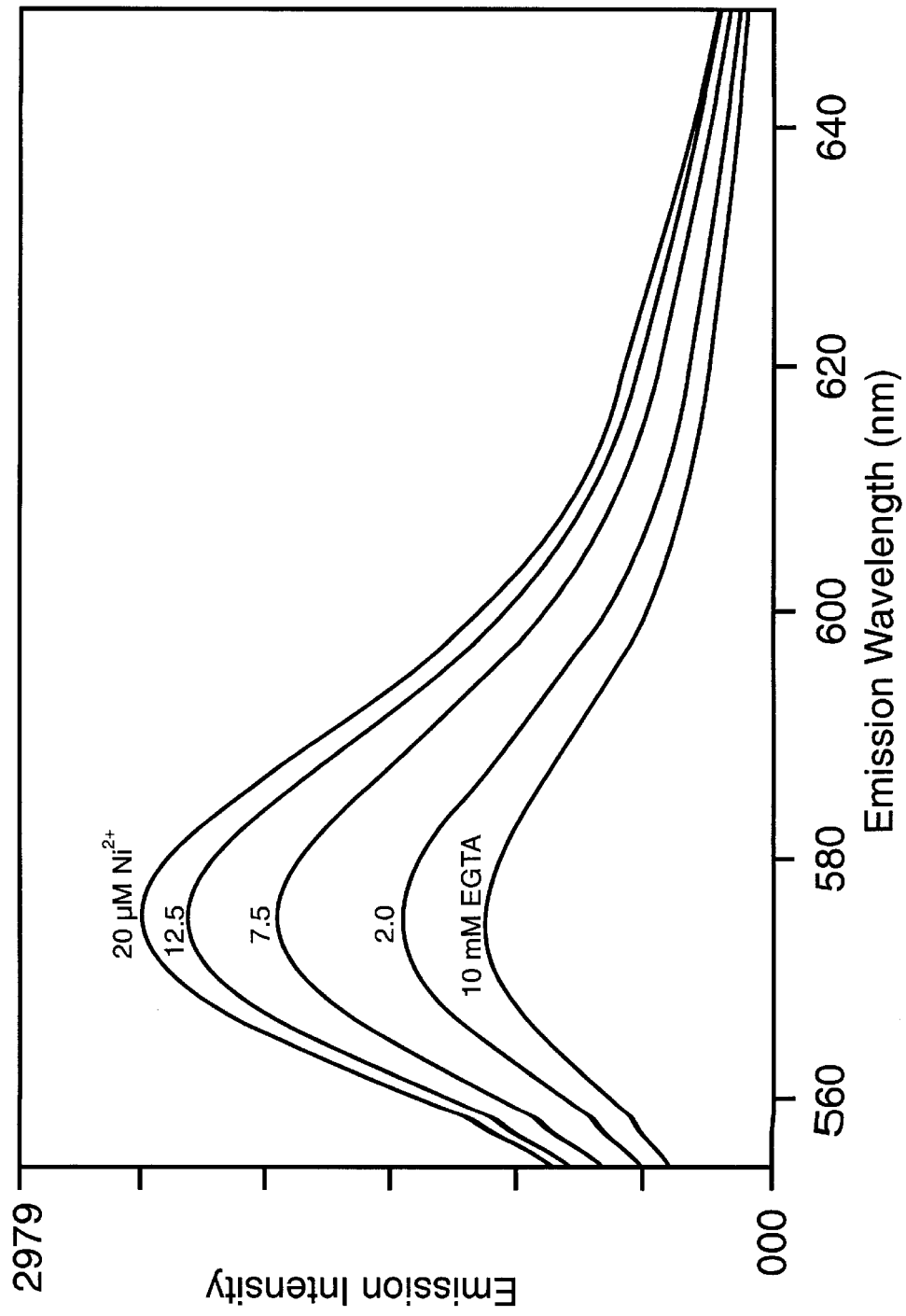
FIG. 6: The relative fluorescence emission intensity of a tetramethylrhodamine bis-pyridyl conjugate in response to concentrations of $Ni^{2+}$ from 0 to 20 $\mu$M.
Figure 7:
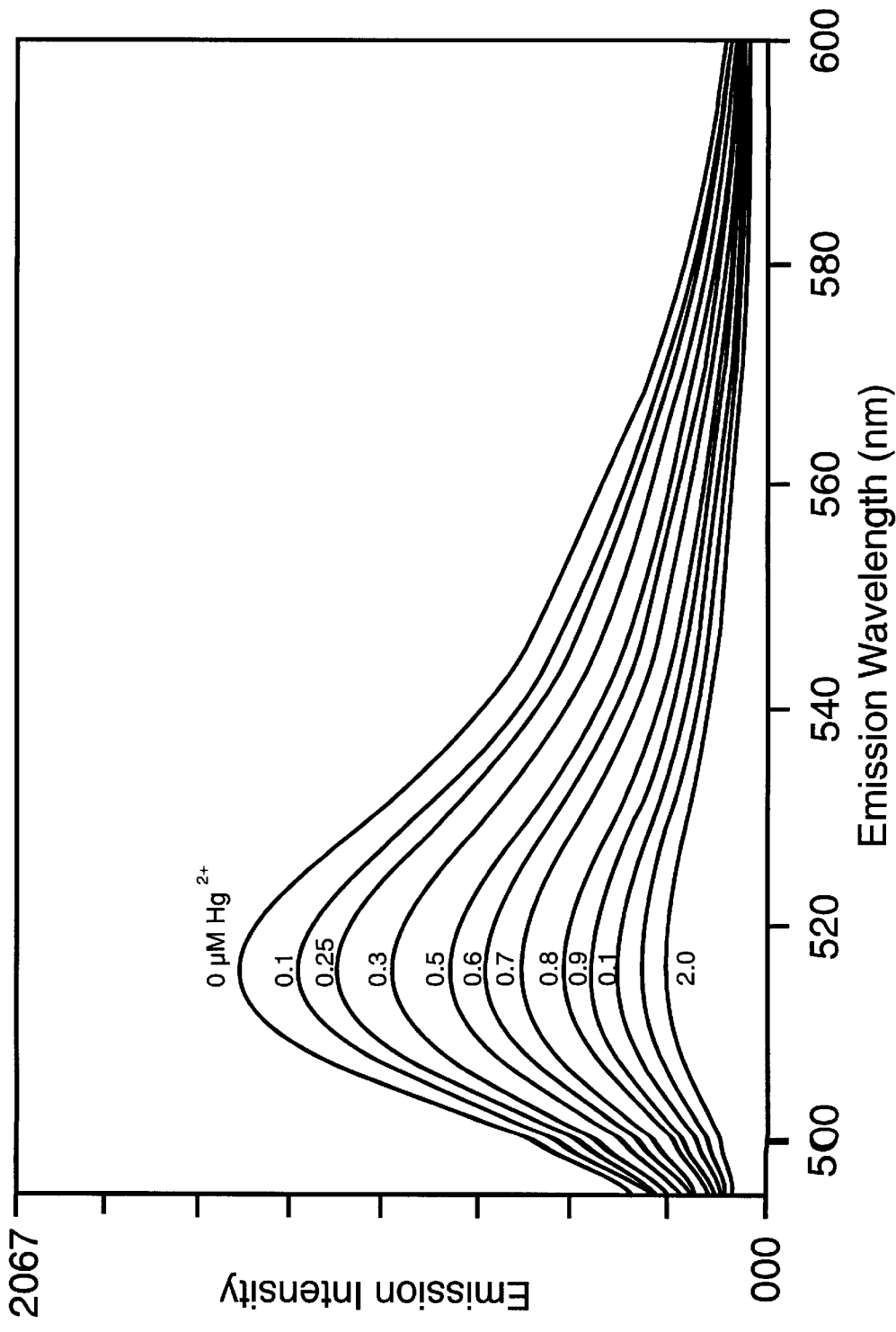
FIG. 7: The decrease in relative fluorescence emission intensity of a fluorescein bis-quinolyl conjugate in response to concentrations of $Hg^{2+}$ from 0 to 20 $\mu$M.
Figure 8:
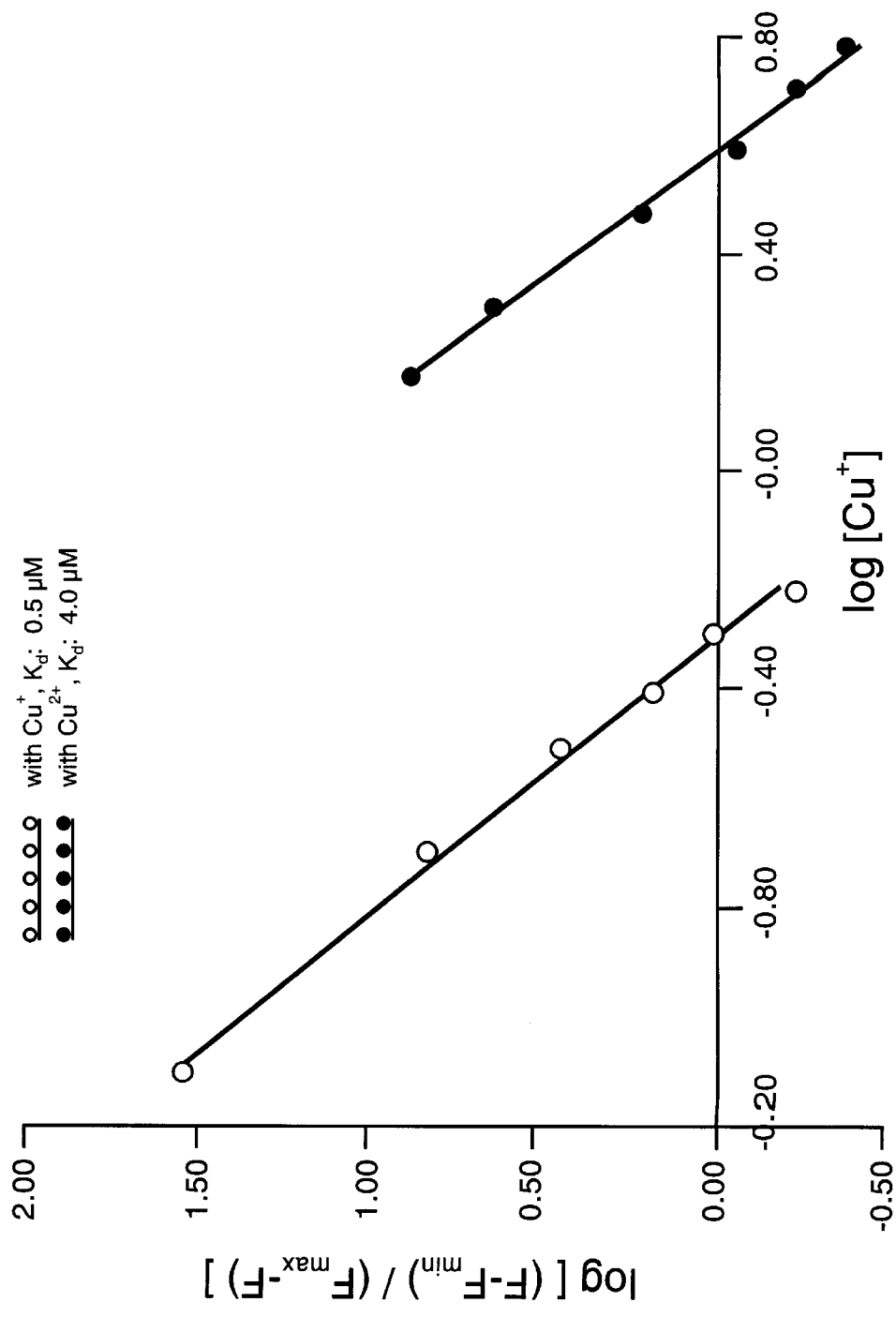
FIG. 8: A comparison of the dissociation constants of a fluorescein conjugate of 5-amino-1,10-phenanthroline for $Cu^{2+}$ ($K_d$=3 $\mu$M) and for $Cu^+$ ($K_d$=0.3 $\mu$M) as described in Example 12.
Figure 9:
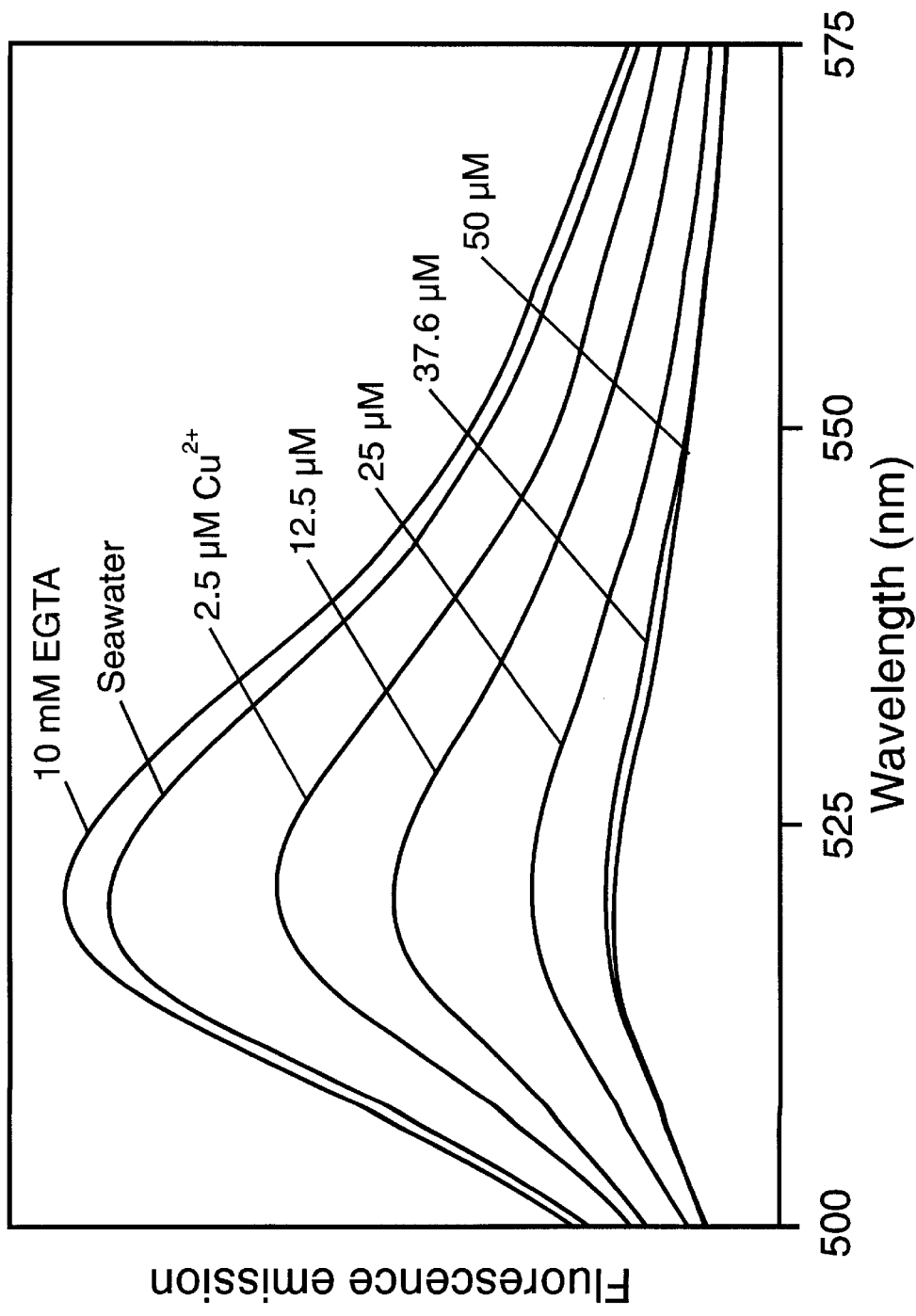
FIG. 9: The fluorescent response of a green fluorescent conjugate of 5-amino-1,10-phenanthroline to $Cu^{2+}$ added to fresh seawater as described in Example 13.

A solution of the mono-protected amine (3.0 g, 14.4 mmoles) in DMF is heated at 100° C. with 2-picolyl chloride (5.2 g, 32 mmoles), sodium iodide (4.75 g, 32 mmoles) and N,N-diisopropylethyl amine (9.3 g, 72 mmoles). After 24 hours, the reaction mixture is diluted with ethyl acetate and washed with saturated NaCl, followed by evaporation, to give a dark oil that is further purified on a silica gel column. Pure fractions are combined and evaporated to yield a tan foam (2.7 g, 48% yield). The foam is dissolved in 25 mL trifluoroacetic acid under argon, left at room temperature for 45 minutes, then evaporated. The residue is dissolved in 50 mL water and enough $NH_4OH$ is added to bring the pH to 10. The resulting solution is extracted with 75 mL chloroform, evaporated and crystallized from 10 mL ethyl acetate to give the free amine as a crystalline solid (1.9 g, 94% yield). This amine can be treated with amine-reactive fluorescent dyes, such as fluorescein-5-isothiocyanate, to give a green-fluorescent indicator (see FIGS. 2 and 4), or treated with an amine-reactive tetramethylrhodamine isothiocyanate to give an orange-fluorescent indicator (see FIG. 6). The method for the conjugation is entirely analogous to that described for fluorescent derivatives of 5-amino-1,10-phenanthroline in Example 1.

Example 7
Fluorescent Bis-quinolyl Indicators Substituted on the Bridge by an Aromatic Spacer Indicators having a bis-quinolyl binding moiety are prepared analogously to the method described in Example 6, excepting that 2-(chloromethyl)quinoline is used in place of 2-picolyl chloride. For example, N'-(t-butyloxycarbonyl)-p-phenylenediamine (0.25 g, 1.2 mmoles) is combined with 2-(chloromethyl)quinoline·HCl (0.51 g, 2.4 mmoles), sodium iodide (0.36 g, 2.4 mmoles) and N,N-diisopropylethylamine (0.78 g, 6.0 mmoles) in 7 mL DMF. The reaction is heated at 80° C. for 14 hours, and then cooled to room temperature. The cooled reaction mixture is then diluted with 50 mL ethyl acetate and washed with 75 mL saturated NaCl before it is evaporated to yield 0.23 g (39% yield). The t-BOC protecting group is removed by dissolving the protected material in 10 mL trifluoroacetic acid at 0° C. The reaction mixture is stirred at room temperature for 30 minutes, then reduced to an oil under reduced pressure and dissolved in 15 mL water. The pH is adjusted to 12 with ammonium hydroxide, and the desired product is extracted into 60 mL ethyl acetate. The organic layer is washed with 150 mL saturated NaCl, and the organic layer is evaporated to give the amine as a dark oil (0.16 g). The amine (82 mg, 0.21 mmoles) is dissolved in 3 mL DMF and fluorescein-5-isothiocyanate (82 mg, 0.21 mmoles) is added in one portion. After 90 minutes, the reaction is evaporated to dryness and purified on silica gel eluting with 90:7:1 chloroform:methanol:acetic acid. Pure fractions are collected, solvent is removed under vacuum, and the resulting residue is dissolved in 2% potassium hydroxide. The resulting red solution is acidified and centrifuged to give the fluorescein bis-quinolyl conjugate as a brown solid (100 mg, 60% yield).

Example 8
bis-Pyridyl Indicators Substituted on the Bridge by an Aliphatic Spacer A solution of mono-(t-butyloxycarbonyl)ethylenediamine (2.0 g, 12.5 mmoles) in 20 mL DMF is combined with 2-chloromethyl-6-methoxyquinoline (5.3 g, 26.2 mmoles) and N,N-diisopropylethylamine (4.9 g, 72 mmoles) and is then heated to 75° C. After 22 hours, the reaction is evaporated to give a dark oil. This is purified by chromatography oil silica gel. Pure fractions are combined and evaporated to give a tan oil (2.6 g, 53% yield).

The oil is then dissolved in 13 mL trifluoroacetic acid under argon for 45 minutes, followed by evaporation of the solvent. The resulting residue is dissolved in 50 mL 10% $NH_4OH$. The crude product is extracted into 75 mL chloroform and evaporated to give a dark oil that is purified by chromatography on silica gel to yield the free amine as a tan solid. To a solution of the amine (50 mg, 0.13 mmoles) in 1.5 mL DMF is added 4-chloro-7-nitrobenz-2-oxa-1,3-diazole (NBD chloride) (25 mg, 0.13 mmoles) and triethylamine (15 $\mu$L). After three hours, the reaction mixture is added to 10 mL water, centrifuged and the resulting pellet is recrystallized from 5 mL methanol to give the green fluorescent conjugate as a dark yellow solid (65 mg, 89% yield).

Fluorescent dyes containing carboxylic acids are conjugated to the aliphatic amine by activation of the acid using standard methods, as described in Example 3. Available amine reactive dyes, such as succinimidyl esters of fluoresceins, rhodamines, rhodols or rosamines can be combined with the amine in DMF to give fluorescent conjugates that are easily purified by chromatography.

Example 9
bis-Pyridyl Indicators Directly Substituted on the Bridge by the Fluorophore A solution of 9-aminoanthracene (1.0 g, 5.1 mmoles) in 20 mL acetonitrile is combined with 2-picolyl chloride (2.0 g, 12.7 mmoles), sodium iodide (0.9 g, 6 mmoles) and N,N-diisopropylethylamine (2.8 g, 20.4 mmoles) and the resulting solution is heated at reflux for 16 hours. The resulting dark solution is evaporated and crystallized from 30 mL methanol to give the bispyridyl-anthracene as a dark solid (1.6 g, 83% yield). Using completely analogous methods, other fluorescent bis-pyridyl indicators can be synthesized starting with a variety of amine-containing fluorescent dyes, such as 7-aminocoumarin-4-acetic acid and 1-aminopyrene.

Example 10
Screening Fluorescent Indicators for their Target Ions

Fluorescent metal-ion indicators are tested for their response to selected metal ions in aqueous solution by the general procedure given below:

A sample of the indicator is first dissolved in pure water to give a dye concentration of 1 mM. This stock solution is then diluted into solutions containing about 1 to about 25 $\mu$M concentrations of selected soluble metal ions to give final dye concentrations between 1 and 10 $\mu$M. The excitation or emission spectrum of each solution is scanned and the excitation or emission intensities and peak wavelengths recorded. These data are compared to those recorded for solutions comprising an equal volume of dye dissolved in a "cation-free" solution of 10 mM EGTA, 100 mM KCl and 10 mM MOPS at pH 7.0. Using this method, metal ions that give a detectable change in fluorescence can be determined. These are then defined as target ions of the indicator and the sensitivity range of these ions determined as described in the following examples. FIG. 1 shows the results of screening 1 $\mu$M solutions of a green fluorescent conjugate of 5-amino-1,10-phenanthroline with a series of metal ions at 25 $\mu$M.

In an analogous fashion, indicators that are not soluble in water can be dissolved at low concentrations in nonpolar solvents such as ethers, esters, ketones, certain alcohols, hydrocarbons or chlorinated hydrocarbons and these solutions can be exposed to metal ions in aqueous solution. The indicators serve to extract the metals into the organic layer, where the fluorescence response of the dye is detected and correlated to metal concentration in the aqueous or solid sample.

Example 11
Determining the Binding Affinity of Indicators for Target Ions

The affinity of fluorescent metal ion indicators is determined for indicators dissolved in homogeneous solution by exposing a selected indicator to increasing concentrations of metal ions and monitoring the fluorescence response using a fluorimeter, microscope, flow cytometer or other instrument capable of detecting a change in fluorescence properties. The change in fluorescence is then plotted versus the metal ion concentration to give a calibration curve of response. Samples having unknown concentrations of metal ion can then be compared against this calibration curve and the metal ion concentration estimated.

Figure 2:
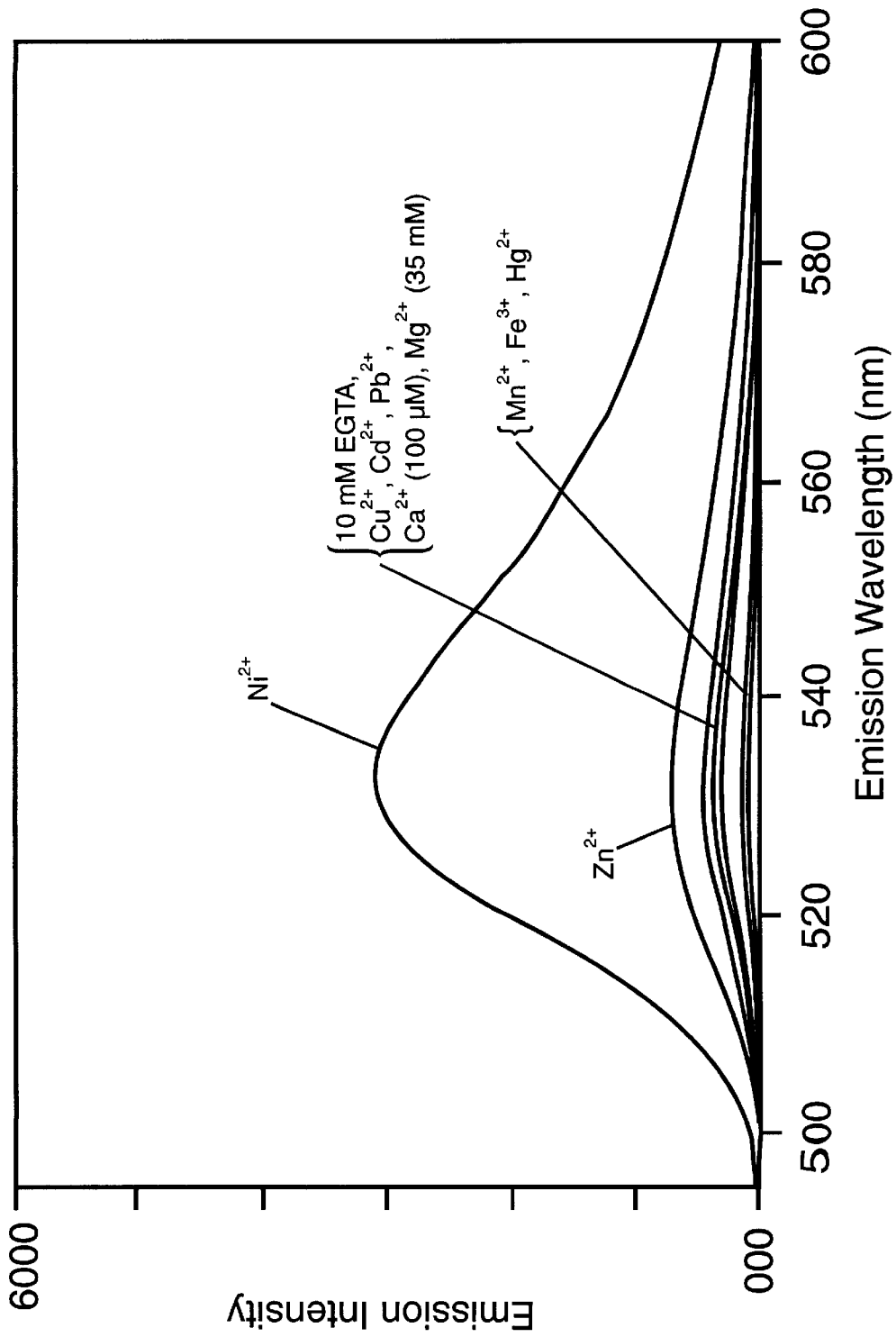
FIG. 2: The relative fluorescence emission intensity of a fluorescein bis-pyridyl conjugate in response to selected metal ions.
Figure 3:
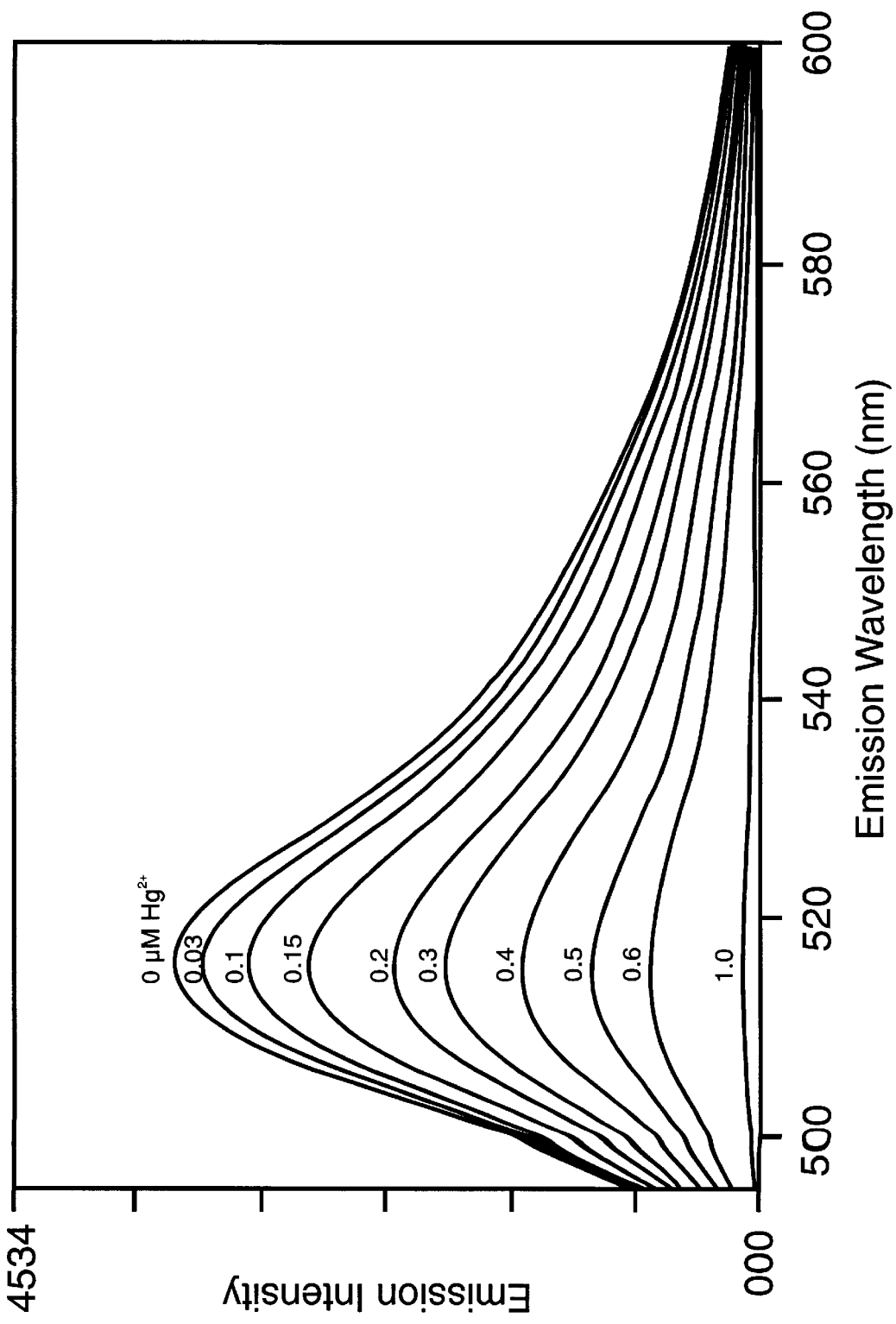
FIG. 3: The fluorescent response of a fluorescein conjugate of 5-amino-1,10-phenanthroline to variable concentrations of $Hg^{2+}$ between 0 and 1 $\mu$M, as described in Example 11.

For example, the binding affinity of a green fluorescent phenanthroline derivative for $Hg^{2+}$ is determined by exposing a 1 $\mu$M solution of the indicator described in Example 1 to concentrations of $HgCl_2$ ranging from a "cation-free" solution (10 mM EGTA) to 1.0 $\mu$M $Hg^{2+}$. The emission intensity decreases in a linear fashion in response to the added metal ion up to 1 $\mu$M metal ion, beyond which there is no further change (as shown in FIG. 2). The decrease in emission intensity can be used to determine the dissociation constant of the indicator using a Hill plot, where the log of the change in fluorescence decrease (log $(F-F_{min}/F_{max}-F)$) is plotted versus the log of the ion concentration (log[$Hg^{2+}$]). The point at which the plot intercepts the x-axis is defined as the half-saturation point for the metal binding of the indicator, and is equal to the dissociation constant. For this indicator, the $K_d(Hg^{2+})$ is found to be 0.3 $\mu$M (as shown in FIG. 3).

Figure 4:
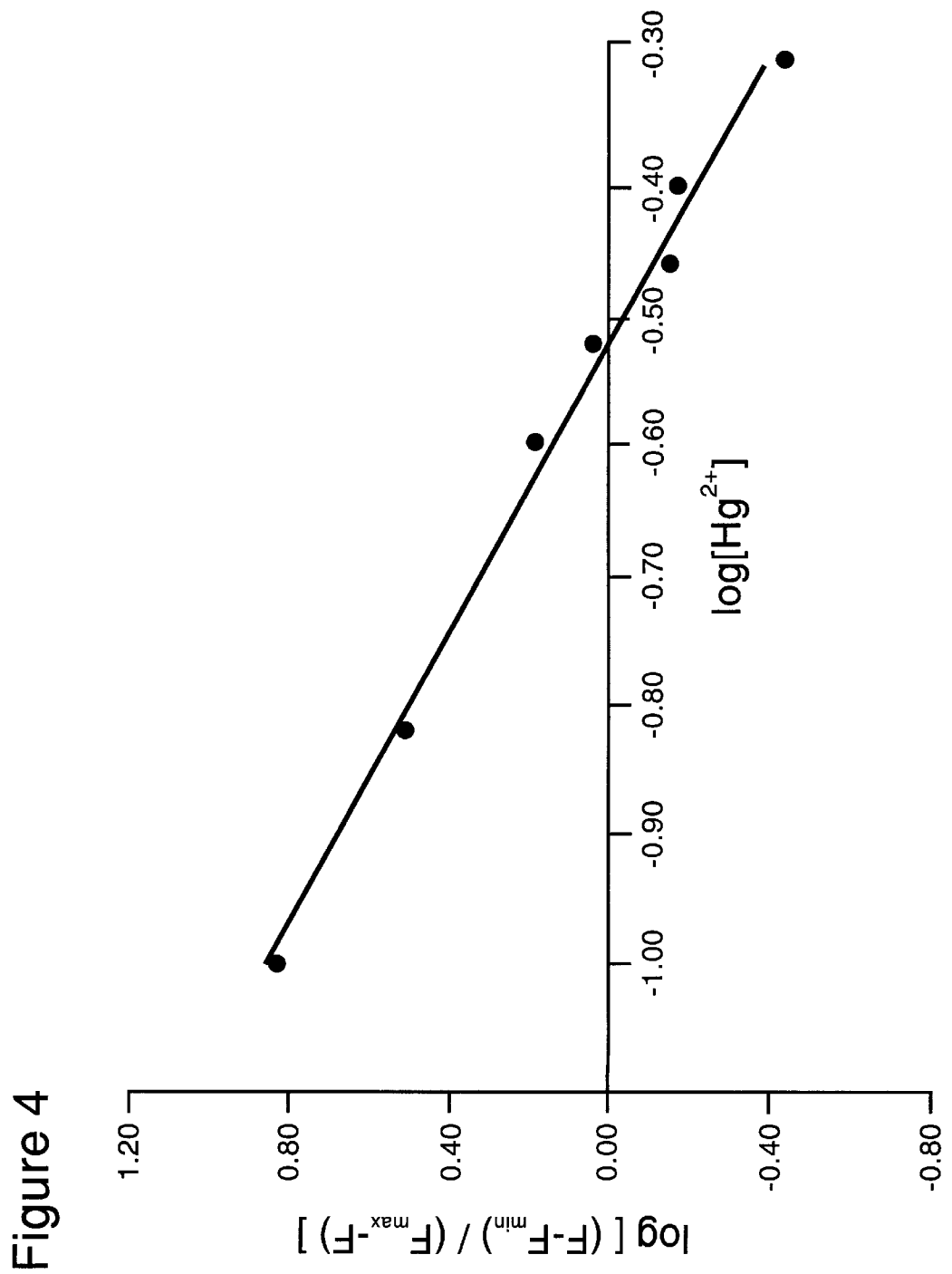
FIG. 4: The determination of the binding affinity of a fluorescein conjugate of 5-amino-1,10-phenanthroline, using a Hill plot of the fluorescence data shown in FIG. 3, as described in Example 11.

Example 12
Determining the Affinity of Indicators for Different Species of Metal Ion The instant indicators can be used to distinguish between the different oxidation states of a metal ion. For example, a solution of a green fluorescent phenanthroline derivative is dissolved in a solution of 5 mM MOPS at pH 7.0 to give a final dye concentration of 1 $\mu$M. The emission spectrum of the free indicator is then scanned from 450 nm to 650 nm while the sample is excited at 488 nm. The peak emission intensity is found to be 515 nm. Subsequent additions of small aliquots of a $CuCl_2$ solution (25 $\mu$M in water) give a series of $Cu^{+2+}$ concentrations from zero (10 mM EGTA) to 10 μM $Cu^{2+}$. The emission intensity decreases in a linear fashion in response to added metal ion. The dissociation constant for $Cu^{2+}$ is found to be 3 μM using the method described in Example 11. Repeating this experiment with aliquots of a $Cu^+$ solution shows that the same indicator has an affinity for $Cu^+$ of 0.3 μM, an order of magnitude higher affinity than for $Cu^{2+}$ (as shown in FIG. 4).

Example 13

Fluorescent Detection of Metal Ions in the Presence of High Salt Concentrations

The metal-ion indicators of the present invention can be used to detect low levels of target ions in the presence of very high concentrations of other mono- and divalent cations. For example, a solution of a green fluorescent phenanthroline derivative (as described in Example 1) is diluted into freshly collected, unfiltered seawater to give a dye concentration of 1 μM. Using 10 mM EGTA, pH 7.20, 100 mM KCL in 10 mM MOPS as a standard, the fluorescence emission of the indicator solution is scanned from 450 nm to 650 nm in a Perkin Elmer PE-450 fluorimeter with excitation at 488 nm. Comparison of the fluorescence response of the indicator in seawater and that of the same concentration of indicator in the EGTA solution shows that 90% of the original fluorescence intensity is retained. The addition of aliquots of $CuCl_2$, with subsequent analysis of the fluorescence response, shows that the fluorescence emission is seen to decrease to approximately 10% of the original emission intensity over the range of zero to 10 μM added $Cu^{2+}$ (as shown in FIG. 5).

Example 14

Visual Detection of Metal Ions

The indicators described in the present invention are useful as sensitive, direct indicators of water quality with little or no instrumentation. For example, a solution of a green fluorescent derivative of phenanthroline is diluted into 2.0 mL of deionized water to a final concentration of 5 μM, resulting in a bright, green fluorescent solution. The same quantity of dye is added to a 2.0 mL sample of 1 μM $Hg^{2+}$ and the two water samples compared visually using ambient light for excitation of the dye. The water sample containing $Hg^{2+}$ is orange in color, while the pure water sample is a bright fluorescent green. The use of a portable UV hand lamp (excitation 350 nm) to illuminate the samples shows that the pure water sample is brightly fluorescent, while the sample containing $Hg^{2+}$ shows no fluorescence emission.

In a similar experiment, the intensity of 5 μM indicator is visually compared in 2.0 mL solutions of deionized water, tap water and well water were compared, with a slight visually observed decrease in fluorescence emission intensity for the tap water, and a strong decrease in emission intensity for the well water, using both ambient light and UV excitation.

It is to be understood that, while the foregoing invention has been described in detail by way of illustration and example, numerous modifications, substitutions, and alterations are possible without departing from the spirit and scope of the invention as described in the following claims.

What is claimed is:

1. A compound containing:

a metal ion-binding moiety, M, having two pyridyl rings, of the formula

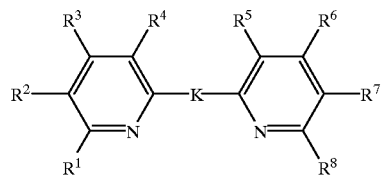

wherein pyridyl ring substituents $R^1$, $R^2$, $R^3$, $R^4$, $R^5$, $R^6$, $R^7$, and $R^8$ are independently H, $C_1$–$C_6$ alkyl, $C_1$–$C_6$ alkoxy, $C_1$–$C_6$ perfluoroalkyl, halogen, CN, sulfonic acid, salt of sulfonic acid, amino, salt of amino, alkylamino having 1–6 carbons, dialkylamino having 2–12 carbons; carboxy, carboxyalkyl having 2–7 carbons, carboxyalkoxy having 2–7 carbons, carboxyalkylthio having 2–7 carbons, carboxyalkoxy having 2–7 carbons, or a 1-(acyloxy)alkyl ester of any such carboxy, such ester having 2–7 carbons; or aryl, or heteroaryl; or —L—$F_L$;

or any two adjacent substituents of $R^1$, $R^2$, $R^3$, $R^4$, $R^5$, $R^6$, $R^7$, and $R^8$, taken into combination, form a fused six-membered aromatic ring, such that no more than one fused ring is bound to each pyridyl ring, and where said fused rings are optionally and independently further substituted by $C_1$–$C_6$ alkyl, $C_1$–$C_6$ alkoxy, $C_1$–$C_6$ perfluoroalkyl, CN, sulfonic acid, salt of sulfonic acid, amino, alkylamino having 1–6 carbons, dialkylamino having 2–12 carbons; carboxy, carboxyalkyl having 2–7 carbons, carboxyalkoxy having 2–7 carbons, carboxyalkylthio having 2–7 carbons, or a 1-(acyloxy)alkyl ester of any such carboxy, such ester having 2–7 carbons; or —L—$F_L$; and K is a single covalent bond, or K is —$(CR^{11}_2)_a$—$NR^{13}_b$—$(CR^{12}_2)_c$—, wherein a, b and c are each 0 or 1, provided that when b=1, a+c must equal 0 or 2;

each $R^{11}$ and $R^{12}$ is optionally and independently H, or $C_1$–$C_6$ alkyl;

$R^{13}$ is H, $C_1$–$C_6$ alkyl, —L—$F_L$, or phenyl that is optionally further substituted by $C_1$–$C_6$ alkyl, $C_1$–$C_6$ alkoxy, $NO_2$, $C_1$–$C_6$ perfluoroalkyl, halogen, CN, sulfonic acid, salt of sulfonic acid, amino, alkylamino having 1–6 carbons, dialkylamino having 2–12 carbons; carboxy, carboxyalkyl having 2–7 carbons, carboxyalkoxy, or a 1-(acyloxy)alkyl ester of any such carboxy, such ester having 2–7 carbons; or —L—$F_L$; or K is

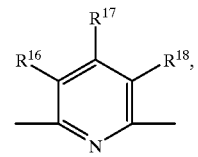

wherein $R^{16}$, $R^{17}$, and $R^{18}$ are independently H, $C_1$–$C_6$ alkyl, $C_1$–$C_6$ alkoxy, $NO_2$, $C_1$–$C_6$ perfluoroalkyl, halogen, CN, sulfonic acid, salt of sulfonic acid, amino, alkylamino having 1–6 carbons, dialkylamino having 2–12 carbons; carboxy, carboxyalkyl having 2–7 carbons, carboxyalkoxy having 2–7 carbons, carboxyalkylthio having 2–7 carbons, or a 1-(acyloxy)alkyl ester of any such carboxy, such ester having 2–7 carbons; or aryl, or heteroaryl, or —L—$F_L$; or K is a formal single bond, and $R^4$ and $R^5$ when taken in combination are —$CR^9$=$CR^{10}$—, forming a phenanthroline moiety, wherein $R^9$ and $R^{10}$ are independently H, $C_1$–$C_6$ alkyl, $C_1$–$C_6$ alkoxy, $C_1$–$C_6$ perfluoroalkyl, CN, sulfonic acid, salt of sulfonic acid, amino, alkylamino having 1–6 carbons, dialkylamino having 2–12 carbons; carboxy, carboxyalkyl having 2–7 carbons, carboxyalkoxy having 2–7 carbons, carboxyalkylthio having 2–7 carbons; or a 1-(acyloxy)alkyl ester of any such carboxy, such ester having 2–7 carbons; or —L—$F_L$; and the remaining ring substituents $R^1$, $R^2$, $R^3$, $R^6$, $R^7$, and $R^8$ are as defined above;

such that at least one but not more than two substituents on said metal ion-binding moiety is —L—$F_L$; wherein each $F_L$ is independently a fluorescein, a rhodol, a rosamine or a rhodamine fluorophore that is attached to said metal-binding moiety by L, where each L is independently a single bond or a covalent linkage that is 9 or fewer non-hydrogen atoms in length.

2. A compound containing a metal ion-binding moiety, M, having two pyridyl rings, of the formula

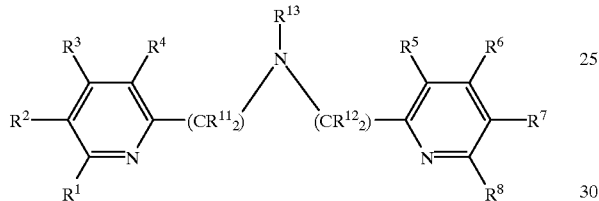

wherein pyridyl ring substituents $R^1$, $R^2$, $R^3$, $R^4$, $R^5$, $R^6$, $R^7$, and $R^8$ are independently H, $C_1$–$C_6$ alkyl, $C_1$–$C_6$ alkoxy, $C_1$–$C_6$ perfluoroalkyl, halogen, CN, sulfonic acid, salt of sulfonic acid, amino, salt of amino, alkylamino having 1–6 carbons, dialkylamino having 2–12 carbons; carboxy, carboxyalkyl having 2–7 carbons, carboxyalkoxy having 2–7 carbons, carboxyalkylthio having 2–7 carbons, carboxyalkylamino having 2–7 carbons, or a 1-(acyloxy)alkyl ester of any such carboxy, such ester having 2–7 carbons; or aryl, or heteroaryl; or —L—$F_L$;

or any two adjacent substituents of $R^1$, $R^2$, $R^3$, $R^4$, $R^5$, $R^6$, $R^7$, and $R^8$, taken in combination, form a fused six-membered aromatic ring, such that no more than one fused ring is bound to each pyridyl ring, and where said fused rings are optionally and independently further substituted by $C_1$–$C_6$ alkyl, $C_1$–$C_6$ alkoxy, $C_1$–$C_6$ perfluoroalkyl, CN, sulfonic acid, salt of sulfonic acid, amino, alkylamino having 1–6 carbons, dialkylamino having 2–12 carbons; carboxy, carboxyalkyl having 2–7 carbons, carboxyalkoxy having 2–7 carbons, carboxyalkylthio having 2–7 carbons, or a 1-(acyloxy) alkyl ester of any such carboxy, such ester having 2–7 carbons; or —L—$F_L$;

each $R^{11}$ and $R^{12}$ is optionally and independently H, or $C_1$–$C_6$ alkyl;

$R^{13}$ is H, $C_1$–$C_6$ alkyl, —L—$F_L$, or phenyl that is optionally further substituted by $C_1$–$C_6$ alkyl, $C_1$–$C_6$ alkoxy, $NO_2$, $C_1$–$C_6$ perfluoroalkyl, halogen, CN, sulfonic acid, salt of sulfonic acid, amino, alkylamino having 1–6 carbons, dialkylamino having 2–12 carbons, carboxy, carboxyalkyl having 2–7 carbons, carboxyalkoxy, or a 1-(acyloxy)alkyl ester of any such carboxy, such ester having 2–7 carbons; or —L—$F_L$;

such that at least one but not more than two substituents on said metal ion-binding moiety is —L—$F_L$; wherein each $F_L$ is independently a fluorophore that is a fluorescein, a rosamine, a rhodol or a rhodamine that is attached to said metal-binding moiety by L, where each L is independently a single bond or a covalent linkage that is 9 or fewer non-hydrogen atoms in length;

provided that one of substituents $R^1$, $R^2$, $R^3$, $R^4$, $R^5$, $R^6$, $R^7$, $R^8$, and $R^{13}$ is L—$F_L$, or $R^{13}$ is phenyl substituted by —L—$F_L$.

3. A compound, as claimed in claim 2, wherein $R^{13}$ is —L—$F_L$, and each $R^{11}$ and $R^{12}$ is hydrogen.

4. A compound, as claimed in claim 2, wherein $R^{13}$ is —L—$F_L$, and L is —$(CH_2)_n$—, where n=2–6.

5. A compound, as claimed in claim 2, wherein M has the formula

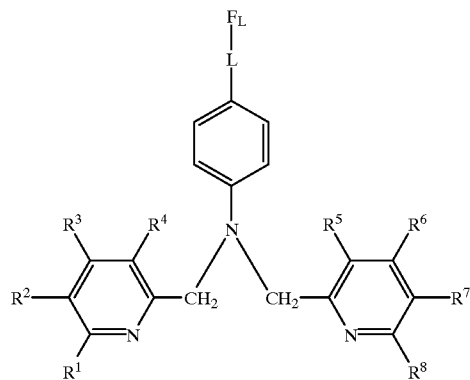

wherein L is a single bond, an alkyl linkage, a phenylene linkage, or an ether, thioether, sulfonamide, carboxamide, alkyl amine, urea, thiourea or aminotriazine linkage.

6. A compound, as claimed in claim 2, wherein the pyridyl ring substituents $R^1$, $R^2$, $R^3$, $R^4$, $R^5$, $R^6$, $R^7$, and $R^8$ are independently hydrogen, sulfonic acid, salt of sulfonic acid, amino, salt of amino, carboxy, carboxyalkyl having 2–7 carbons, carboxyalkoxy having 2–7 carbons, carboxyalkylamino having 2–7 carbons, carboxyalkylthio having 2–7 carbons, or —L—$F_L$.

7. A compound, as claimed in claim 2, wherein the pyridyl ring substituents $R^1$, $R^2$, $R^3$, $R^4$, $R^5$, $R^6$, $R^7$, and $R^8$ are independently hydrogen, alkyl having 1–6 carbons, alkoxy having 1–6 carbons, perfluoroalkyl having 1–6 carbons, CN, amino, alkylamino having 1–6 carbons, dialkylamino having 2–12 carbons, or a 1-(acyloxy)alkyl ester of any carboxy substituent, such ester having 2–7 carbons; or aryl, heteroaryl or —L—$F_L$.

8. A compound, as claimed in claim 2, wherein said covalent linkage is a single bond, an alkyl linkage, a phenylene linkage, or an ether, thioether, sulfonamide, carboxamide, alkyl amine, urea, thiourea or aminotriazine linkage.

9. A compound, as claimed in claim 1, wherein M has the formula

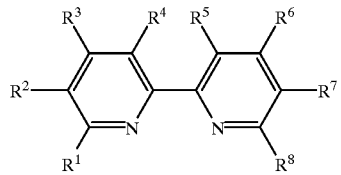

and one of substituents $R^1$, $R^2$, $R^3$, $R^4$, $R^5$, $R^6$, $R^7$, and $R^8$ is —L—$F_L$.

10. A compound as claimed in claim 7, wherein $R^3$ and optionally $R^6$ are —L—$F_L$.

11. A compound, as claimed in claim 8, wherein the pyridyl ring substituents $R^1$, $R^2$, $R^4$, $R^5$, $R^7$, $R^8$, and $R^6$, where $R^6$ is not a fluorophore, are independently hydrogen, sulfonic acid, salt of sulfonic acid, amino, salt of amino, carboxy, alkyl having 1–6 carbons, or alkoxy having 1–6 carbons, provided that no more than three of the ring substituents $R^1$, $R^2$, $R^4$, $R^5$, $R^7$, $R^8$, and $R^6$ are not hydrogen; and wherein each fluorophore is independently linked to the metal-binding moiety by a covalent linkage that is a single bond, an alkyl linkage, a phenylene linkage, a sulfonamide, a carboxamide, an alkyl amine, or a thiourea.

12. A compound as claimed in claim 1, wherein M has the formula

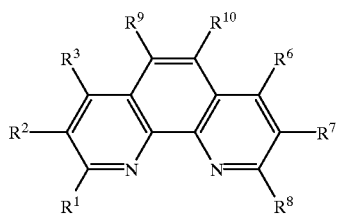

and one of substituents $R^1$, $R^2$, $R^3$, $R^6$, $R^7$, $R^8$, $R^9$ and $R^{10}$ is —L—$F_L$.

13. A compound, as claim in claim 12, wherein $R^9$ is —L—$F_L$.

14. A compound, as claimed in claim 11, wherein the substituents $R^1$, $R^2$, $R^3$, $R^6$, $R^7$, $R^8$, and $R^{10}$ are independently hydrogen, sulfonic acid, salt of sulfonic acid, amino, salt of amino, carboxy, alkyl having 1–6 carbons, or alkoxy having 1–6 carbons, provided that no more than three of the ring substituents $R^1$, $R^2$, $R^3$, $R^6$, $R^7$, $R^8$ and $R^{10}$ are not hydrogen; and wherein the fluorophore is independently linked to the metal-binding moiety by a covalent linkage that is a single bond, an alkyl linkage, a phenylene linkage, a sulfonamide, a carboxamide, an alkyl amine, or a thiourea linkage.

15. A compound, as claimed in claim 2, wherein the pyridyl ring substituents $R^1$, $R^2$, $R^3$, $R^4$, $R^5$, $R^6$, $R^7$, and $R^8$ are independently hydrogen, sulfonic acid, salt of sulfonic acid, amino, salt of amino, carboxy, alkyl having 1–6 carbons, or alkoxy having 1–6 carbons; provided that no more than three of the ring substituents $R^1$, $R^2$, $R^3$, $R^4$, $R^5$, $R^6$, $R^7$, and $R^8$ are not hydrogen;

each $R^{11}$ and $R^{12}$ is hydrogen;

$R^{13}$ is L—$F_L$, or $R^{13}$ is phenyl substituted by —L—$F_L$;

wherein the fluorophore is independently linked to the metal-binding moiety by a covalent linkage that is a single bond, an alkyl linkage, a phenylene linkage, a sulfonamide, a carboxamide, an alkyl amine, or a thiourea linkage.

16. A compound, as claimed in claim 1, wherein M has the formula

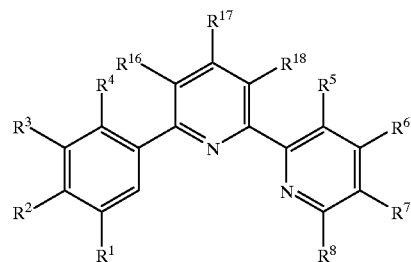

and one of $R^1$, $R^2$, $R^3$, $R^4$, $R^5$, $R^6$, $R^7$, $R^8$, $R^{16}$, $R^{17}$ and $R^{18}$ is —L—$F_L$.

17. A compound, as claimed in claim 16, wherein $R^{17}$ is —L—$F_L$.

18. A compound, as claimed in claim 17, wherein the substituents $R^1$, $R^2$, $R^3$, $R^4$, $R^5$, $R^6$, $R^7$, $R^8$, $R^{16}$ and $R^{18}$ are independently hydrogen, sulfonic acid, salt of sulfonic acid, amino, salt of amino, carboxy, alkyl having 1–6 carbons, or alkoxy having 1–6 carbons; provided that no more than three of the ring substituents $R^1$, $R^2$, $R^3$, $R^4$, $R^5$, $R^6$, $R^7$, $R^8$, $R^{16}$, and $R^{18}$ are not hydrogen;

wherein the fluorophore is independently linked to the metal-binding moiety by a covalent linkage that is a single bond, an alkyl linkage, a phenylene linkage, a sulfonamide, a carboxamide, an alkyl amine, or a thiourea linkage.

* * * * *

UNITED STATES PATENT AND TRADEMARK OFFICE
CERTIFICATE OF CORRECTION

PATENT NO. : 6,013,802  
DATED : January 11, 2000  
INVENTOR(S) : Hoyland et al.

It is certified that error appears in the above-identified patent and that said Letters Patent is hereby corrected as shown below:

Column 1,  
Line 14, "Tile" should read -- The --.

Column 11,  
Table 1, "alcohols/pheriols" should read -- alcohol/phenol --.

Column 14,  
Line 27, "all" should read -- an --.

Column 18,  
Line 46, "are" should read -- arc --.

Column 26,  
Line 18, "carboxyalkoxy" should read -- carboxyalkylamino --.  
Line 48, delete "or" following ";"

Signed and Sealed this

Twenty-fourth Day of September, 2002

Attest:

Attesting Officer

JAMES E. ROGAN  
*Director of the United States Patent and Trademark Office*